US006465716B2

(12) United States Patent
Etzler et al.

(10) Patent No.: US 6,465,716 B2
(45) **Date of Patent: *Oct. 15, 2002**

(54) NOD FACTOR BINDING PROTEIN FROM LEGUME ROOTS

(75) Inventors: Marilynn E. Etzler, Davis, CA (US); Judith B. Murphy, Davis, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/129,112

(22) Filed: Aug. 4, 1998

(65) Prior Publication Data

US 2002/0019995 A1 Feb. 14, 2002

Related U.S. Application Data

(63) Continuation of application No. 08/907,226, filed on Aug. 6, 1997.

(51) Int. Cl.[7] .......................... A01H 5/00; C12N 15/59; C12N 15/52; C12N 15/82

(52) U.S. Cl. ....................... 800/278; 800/287; 800/298; 800/290; 536/23.2; 536/23.6; 435/468; 435/469

(58) Field of Search ........................... 435/4, 69.1, 468, 435/410, 419; 536/23.1, 23.6; 800/278, 290, 295, 298, 287

(56) References Cited

PUBLICATIONS

Roberts et al (1999) A Nod factor–binding lectin is a member of a distinct class of apyrases that may be unique to the legumes. Mol. Gen. Genet. 262:261–267.*

Etzler et al (1999) A nod factor binding lectin with apyrase activity from legume roots. Proc. Natl. acad. Sci. USA 96:5856–5861.*

Hsieh et al. Plant Molecular Biology. 1996. Jan. issue. vol. 30: 135–147.*

* cited by examiner

*Primary Examiner*—Amy J. Nelson
*Assistant Examiner*—Anne Kubelik
(74) *Attorney, Agent, or Firm*—Townsend & Townsend & Crew LLP

(57) ABSTRACT

The present invention provides NBP46 polynucleotides that are useful in modulating Nod factor binding and other plant functions.

21 Claims, 4 Drawing Sheets

NOD FACTOR BINDING PROTEIN FROM LEGUME ROOTS

CROSS REFERENCE TO RELATED APPLICATIONS

This is a continuation in part of U.S. Ser. No. 08/907,226, filed Aug. 6, 1997, which is incorporated herein by reference.

FEDERALLY SPONSORED RESEARCH OR DEVELOPMENT

This invention was made with Government support under Grant No. GM21882, awarded by the National Institutes of Health and under Grant No. DCB 9004967, awarded by the National Science Foundation. The Government has certain rights in this invention.

BACKGROUND OF THE INVENTION

Usable nitrogen is the major limiting nutrient in crop plant growth. Plants derive most of their nutrients including nitrogen from the soil through uptake in the root system. Although most of the nitrogen in the soil is in the form of ammonium ions which is rapidly converted to usable nitrates by bacteria in the soil, the harvesting of plants results in a steady decrease of nitrogen from the soil. Unless the soil is augmented with nitrogen-containing compounds, the soil becomes depleted of usable nitrogen and only atmospheric nitrogen remains.

Legumes, unlike other higher plants, are able through a symbiotic relationship with bacteria to utilize atmospheric nitrogen in the soil. The bacteria, Rhizobia, infect leguminous seedlings and induce nodulation, the end result being the presence within the root system of nodules which contain the rhizobial bacteroids. Once within the root system, the bacteroids are able to "fix" atmospheric nitrogen into organic compounds the legumes can use. In exchange for the conversion of atmospheric nitrogen, the plants provide the bacteroids with carbon-containing compounds, other nutrients, and a protective environment.

Although the "fixed" nitrogen is used throughout the plant in the growth and development of its organs and tissues, much of the usable nitrogen remains within the nodules of the roots. This empirical finding has led to the practice of crop rotation wherein a non-leguminous plant, i.e., corn, is grown and harvested and then the field is sown with a legume, such as alfalfa. After harvest of the legume, the remaining roots are plowed under and thus, usable nitrogen is returned to the soil for the sowing of the non-leguminous crop.

The legumes recognize the rhizobial bacteria through a lectin-carbohydrate interaction. Within the root system, the plants contain lectins that bind to specific carbohydrates found on the Rhizobium cell wall. This interaction is very specific; with each plant recognizing and being infected by one rhizobial strain.

In addition to their involvement in recognition of rhizobial bacteria, oligosaccharide signaling events play important roles in the regulation of plant development, defense, and other interactions of plants with the environment (Ryan, C. A. and Farmer, E. E. *Annu. Rev. Plant Physiol. Plant Mol. Bio.* 42:651–674 (1991); Cote, F. and Hahn, M. G. *Plant Mol. Biol* 26:1379–1411 (1994); Denarie, I. et al. *Annu. Rev. Biochem.* 65:503–535 (1996)). Although the structures of some of these oligosaccharides have been characterized, little is known about the plant receptors for these signals, nor the mechanism(s) by which these signals are transduced.

Previously, a root lectin, NBP46 (formerly called DB46), was isolated from young *Dolichos biflorus* root extracts. NBP46 is a 46 kDa protein that was isolated by affinity chromatography on hog gastric mucin blood group A+H substance conjugated to Sepharose (Quinn, J. M. and Etzler, M. E. *Arch. Biochem. Biophys.* 258:535–544 (1987)).

Identification and characterization of protein and the genes that encode them is important to modulation of oligosaccharide signaling in plants. For instance, a transgenic non-leguminous plant containing a factor that allows rhizobial bacteria to infect the plant and fix nitrogen would lessen the need for the addition of nitrogen-containing fertilizer to soil and preclude the necessity of crop rotation in nitrogen-depleted fields. This would lead to higher yields of crop plants in areas of the world where the soil has been overplanted and replenishment of the depleted soil with usable nitrogen. The present invention addresses these and other needs.

SUMMARY OF THE INVENTION

This invention provides for the isolation and cloning of the cDNA of NBP46 (SEQ ID NO:1), which encodes NBP46, a Nod factor binding lectin. Nod factors are carbohydrates on the surface of Rhizobium which bind to lectins on the surface of leguminous plant organs and can initiate nodulation of the root system by the plants. The NBP46 gene encodes a polypeptide of between 50 and 560 amino acids, more preferably 462 amino acids (SEQ ID NO:2).

In a preferred embodiment, the NBP46 coding sequence is operably linked to a plant specific promoter, more preferably a root specific promoter, such as the NBP46 promoter (SEQ ID NO:3).

In another embodiment, an expression cassette comprising the NBP46 gene is introduced into a transgenic plant. In a preferred embodiment, the expression of NBP46 by the transgenic plant confers to the plant the ability to bind to rhizobial bacteria and utilize atmospheric nitrogen. In a particularly preferred embodiment, the expression of NBP46 confers to the plant the ability to catalyze the hydrolysis of the phosphoanhydride bonds of di- and tri-phosphates, leading to greater availability of nutrients to the plant.

In a further embodiment of the instant invention, methods of modulating the rhizobial interactions and in the phosphatase activity in plants by the introduction of an expression cassette comprising NBP46 are disclosed.

BRIEF DESCRIPTION OF THE FIGURES

In FIG. 1 A, the legend is as follows: HBG A+H (■); human ovarian cyst blood group A substance (♦); human ovarian cyst blood group H substance (▼); de-N-acetylated HBG A+H (●).

In FIG. 1 B, the legend is as follows: *Bradyrhizobium japonicum* USDA110 Nod factor (■); β-O-methyl galactose β(1–3) N-acetyl-D-glucosamine (O); methyl α-N-acetyl-D-glucosamine (●); methyl β-N-acetyl-D-glucosamine (♦); dimer (Δ), trimer (□), and tetramer (O) of β(1–4) N-acetyl-D-glucosamine.

DETAILED DESCRIPTION OF THE INVENTION

I. Definitions

Figure 1A:
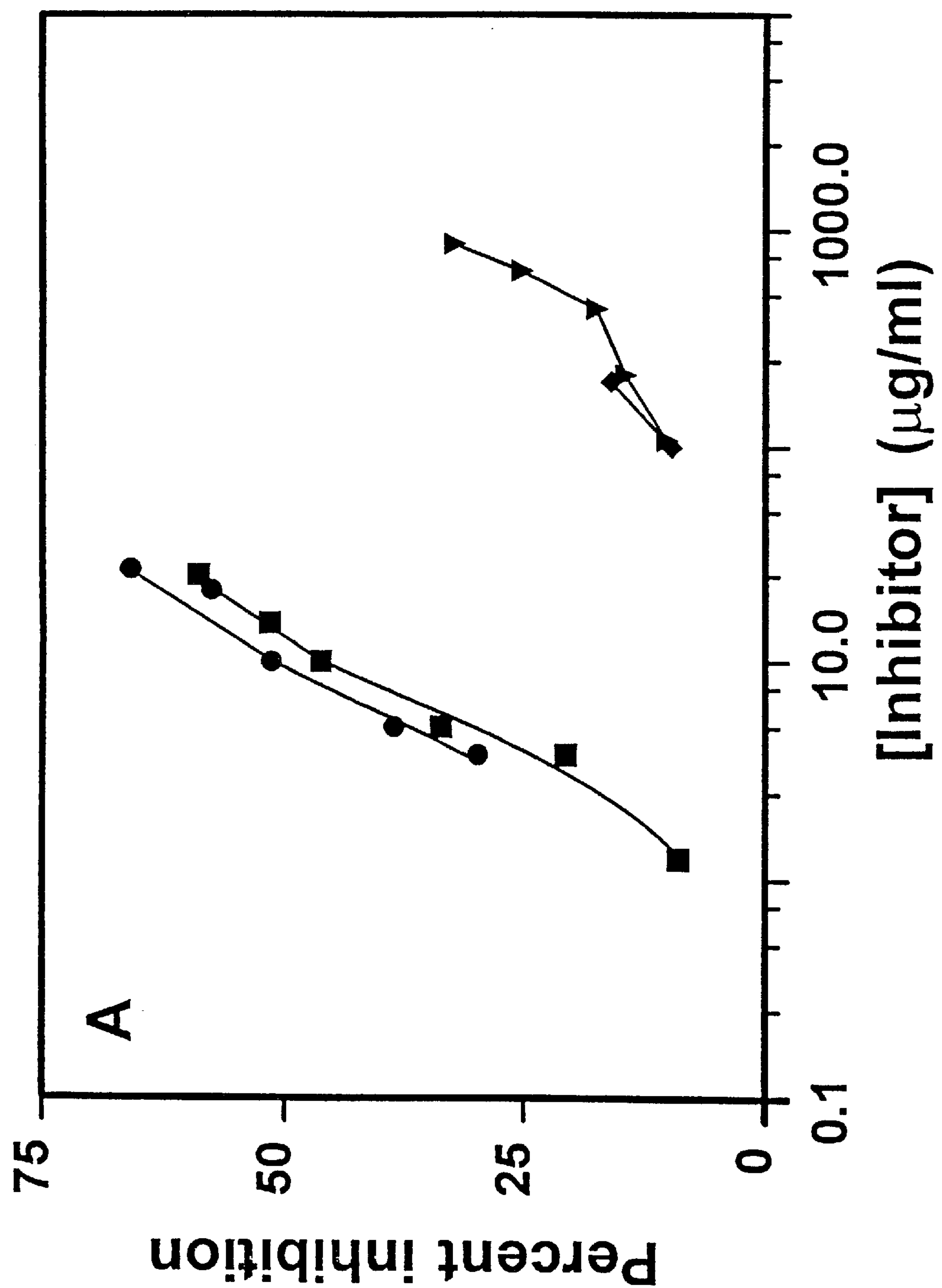
FIG. 1 indicates the inhibition of binding of $^{125}$I-NBP46 to HBG A+H-Sepharose®.

The phrase "isolated nucleic acid molecule" or "isolated protein" refers to a nucleic acid or protein which is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated NBP46 gene is separated from open reading frames which flank the gene and encode a protein other than NBP46. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

A "promoter" is defined as an array of nucleic acid control sequences that direct transcription of an operably linked nucleic acid. As used herein, a "plant promoter" is a promoter that functions in plants. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "plant" includes whole plants, plant organs (e.g., leaves, stems, flowers, roots, etc.), seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant by any means other than by a sexual cross. Examples of means by which this can be accomplished are described below, and include Agrobacterium-mediated transformation, biolistic methods, electroporation, and the like. Such a plant containing the exogenous nucleic acid is referred to here as an R$_1$ generation transgenic plant. Transgenic plants which arise from sexual cross or by selfing are descendants of such a plant.

The phrase "rhizobial binding" refers to the binding between rhizobial bacteria and plant cells. Typically, enhanced binding leads to infection by rhizobial bacteria of the roots of plants. This in turn leads to nodule formation in the roots. For example, a non-leguminous transgenic plant comprising a polynucleotide of this invention and expressing its corresponding polypeptide in the roots of the plant would bind to Nod factors of rhizobial bacteria allowing the plant to become infected by the rhizobial bacteria and allowing the plant to reduce the atmospheric nitrogen contained in the soil and using it as a nutrient.

The phrase "operably linked" refers to a functional linkage between a promoter and a second sequence, wherein the promoter sequence initiates transcription of RNA corresponding to the second sequence.

The term "polynucleotide," "polynucleotide sequence" or "nucleic acid sequence" refers to deoxyribonucleotides or ribonucleotides and polymers thereof in either single- or double-stranded form. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular NBP46 nucleic acid sequence of this invention also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); and Cassol et al., 1992; Rossolini et al., *Mol. Cell. Probes* 8:91–98 (1994)). The term nucleic acid is used interchangeably with gene, cDNA, and mRNA encoded by a gene.

A "NBP46 polynucleotide" is a nucleic acid sequence comprising (or consisting of) a coding region of about 100 to about 2000 nucleotides, sometimes from about 1400 to about 1500 nucleotides, which hybridizes to SEQ ID NO:1 under stringent conditions (as defined below), or which encodes a NBP46 polypeptide.

The term "sexual reproduction" refers to the fusion of gametes to produce seed by pollination. A "sexual cross" is pollination of one plant by another. "Selfing" is the production of seed by self-pollinization, i.e., pollen and ovule are from the same plant.

In the case of both expression of transgenes and inhibition of endogenous genes (e.g., by antisense, or sense suppression) one of skill will recognize that the inserted polynucleotide sequence need not be identical, but may be only "substantially identical" to a sequence of the gene from which it was derived. As explained below, these substantially identical variants are specifically covered by the term NBP46 nucleic acid.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "NBP46 nucleic acid". In addition, the term specifically includes those sequences substantially identical (determined as described below) with an NBP46 polynucleotide sequence disclosed here and that encode polypeptides that are either mutants of wild type NBP46 polypeptides or retain the function of the NBP46 polypeptide (e.g., resulting from conservative substitutions of amino acids in the NBP46 polypeptide). In addition, variants can be those that encode dominant negative mutants as described below.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60%, preferably 80%, most preferably 90–95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

(see, e.g., Creighton, *Proteins* (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

In the present invention, genomic DNA or cDNA comprising NBP46 nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2× SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

The phrase "transgenic plant" refers to a plant into which heterologous polynucleotides have been introduced by any means other than sexual cross or selfing. Examples of means by which this can be accomplished are described below, and include Agrobacterium-mediated transformation, biolistic methods, electroporation, in planta techniques, and the like. Such a plant containing the heterologous polynucleotides is referred to here as an $R_1$ generation transgenic plant. Transgenic plants may also arise from sexual cross or by selfing of transgenic plants into which heterologous polynucleotides have been introduced.

II. Introduction

The present invention provides polynucleotides referred to here as NBP46 polynucleotides, as exemplified by SEQ ID NO:1. Polypeptides encoded by the genes of the invention are lectins involved in binding a variety of carbohydrates. In addition, polypeptides function as an enzyme, catalyzing the dephosphorylation of nucleotide di- and triphosphates. As explained below, the nucleic acid sequences of the invention code for a Nod factor binding lectin naturally expressed in the root tissue of leguminous plants.

The polypeptides of the invention are also involved oligosaccharide signaling events that play important roles in the regulation of plant development, defense, and other interactions of plants with the environment. Although the structures of some of these oligosaccharides have been characterized in the prior art, little is known about the plant receptors for these signals, nor the mechanism(s) by which these signals are transduced. The results presented below show that polyepetides of the invention serve as receptors in oligosaccharide signaling.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook, et al.

III. Isolation Of Nucleic Acid Sequences From Plants

The isolation of sequences from the genes of the invention may be accomplished by a number of techniques. For instance, oligonucleotide probes based on the nucleic acid and peptide sequences disclosed herein can be used to identify the desired gene in a cDNA or genomic DNA library from a desired leguminous plant species. To construct genomic libraries, large segments of genomic DNA are generated by random fragmentation, e.g., using restriction endonucleases, and are ligated with vector DNA to form concatemers that can be packaged into the appropriate vector. To prepare a library of tissue-specific cDNAs, mRNA is isolated from tissues and a cDNA library which contains the gene transcripts is prepared from the mRNA.

The cDNA or genomic library can then be screened using a probe based upon the sequence of a cloned gene such as the polynucleotides disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology can be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes known to those of skill.

Appropriate primers and probes for identifying NBP46 genes from *Dolichos biflorus* or transgenic plant tissues are generated from comparisons of the sequences provided herein. For a general overview of PCR see PCR PROTOCOLS: A GUIDE TO METHODS AND APPLICATIONS, (Innis, M, Gelfand, D., Sninsky, J. and White, T., eds.), Academic Press, San Diego (1990). Appropriate degenerate primers for this invention include, for instance: a 5' PCR primer [5'-TA(T/C)GCNGTNAT(T/C)TT(T/C)GATGC-3'] (SEQ ID NO:4) and a 3' PCR primer [5'-AT(A/G)TT(A/G)TA(T/A/G)AT(G/A)CCNGG-3'] (SEQ ID NO:5) where N denotes all nucleotides. The amplification conditions are typically as follows. Reaction components: 10 mM Tris-HCl, pH 8.3, 50 mM potassium chloride, 1.5 mM magnesium chloride, 0.001% gelatin, 200 $\mu$M dATP, 200 $\mu$M dCTP, 200 $\mu$M dGTP, 200 $\mu$M dTTP, 0.4 $\mu$M primers, and 100 units per mL Taq polymerase. Program: 96° C. for 3 min., 30 cycles of 96° C. for 45 sec., 50° C. for 60 sec., 72° C. for 60 sec, followed by 72° C. for 5 min.

Using the above primers, a partial coding sequence will be obtained. There are many techniques known to those of skill to determine and isolate the complete coding sequence. These methods include using the PCR amplified subsequence to probe a cDNA library for longer sequences.

A preferred method is RACE (Frohman, et. al., *Proc. Nat'l. Acad. Sci. USA* 85:8998 (1988)). Briefly, this technique involves using PCR to amplify a DNA sequence using a random 5' primer and a defined 3' primer, e.g., (SEQ ID NO:6) (5' RACE) or a random 3' primer and a defined 5' primer, e.g., (SEQ ID NO:7) (3' RACE). The amplified sequence is then subcloned into a vector where it is then sequenced using standard techniques. Kits to perform RACE are commercially available (e.g. 5' RACE System, GIBCO BRL, Grand Island, N.Y., USA). In this manner, the entire NBP46 coding sequence of about 1600 bp can be obtained (SEQ ID NO:1). The invention also provides genomic sequence of the NBP46 (SEQ ID NO:3).

Alternatively, primers can be selected and synthesized by those of skill from the cDNA sequence disclosed in SEQ ID NOs:1 and 3.

Polynucleotides may also be synthesized by well-known techniques as described in the technical literature. See, e.g., Carruthers, et al., *Cold Spring Harbor Symp. Quant. Biol.* 47:411–418 (1982), and Adams, et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

IV. Use Of Nucleic Acids Of The Invention To Modulate Gene Expression

The polynucleotides of the invention can be used to enhance expression (i.e., increase expression of an endogenous gene or provide NBP46 expression in a plant that does not normally express NBP46) of genes of the invention and thereby enhance infection of transgenic plants by rhizobial bacteria, increase the level of nutrients taken up by the plants, and affect the growth and development of transgenic plants. Alternatively, enhanced expression can be used to modulate oligosaccharide signaling in the plant. This can be accomplished by the overexpression of NBP46 polypeptides in the tissues of transgenic plants.

The heterologous NBP46 polynucleotides do not have to code for exact copies of the NBP46 proteins exemplified herein. Modified NBP46 polypeptide chains can also be readily designed utilizing various recombinant DNA techniques well known to those skilled in the art and described for instance, in Sambrook et al., supra. Hydroxylamine can also be used to introduce single base mutations into the coding region of the gene (Sikorski, et al., *Meth. Enzymol.* 194: 302–318 (1991)). For example, the chains can vary from the naturally occurring sequence at the primary structure level by amino acid substitutions, additions, deletions, and the like. These modifications can be used in a number of combinations to produce the final modified protein chain.

Alternatively, the nucleic acid sequences of the invention can be used to inhibit expression of an endogenous gene. One of skill will recognize that a number of methods can be used to inactivate or suppress NBP46 activity or gene expression. The control of the expression can be achieved by introducing mutations into the gene or using recombinant DNA techniques. These techniques are generally well known to one of skill and are discussed briefly below.

Methods for introducing a genetic mutations into a plant genes are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, for example, X-rays or gamma rays can be used. Desired mutants are selected by assaying for increased seed mass, oil content and other properties.

Gene expression can be inactivated using recombinant DNA techniques by transforming plant cells with constructs comprising transposons or T-DNA sequences. NBP46 mutants prepared by these methods are identified according to standard techniques. For instance, mutants can be detected by PCR or by detecting the presence or absence of NBP46 mRNA, e.g., by Northern blots. Mutants can also be selected by assaying for increased seed mass, oil content and other properties.

The isolated sequences prepared as described herein, can also be used in a number of techniques to suppress endogenous NBP46 gene expression. A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA,* 85:8805–8809 (1988), and Hiatt et al., U.S. Pat. No. 4,801,340.

The nucleic acid segment to be introduced generally will be substantially identical to at least a portion of the endogenous NBP46 gene or genes to be repressed. The sequence, however, need not be perfectly identical to inhibit expression. The vectors of the present invention can be designed such that the inhibitory effect applies to other genes within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 1700 nucleotides is especially preferred.

Catalytic RNA molecules or ribozymes can also be used to inhibit expression of NBP46 genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAS) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature,* 334:585–591 (1988).

Another method of suppression is sense cosuppression. Introduction of nucleic acid configured in the sense orientation has been recently shown to be an effective means by which to block the transcription of target genes. For an example of the use of this method to modulate expression of endogenous genes see, Napoli et al., *The Plant Cell* 2:279–289 (1990), and U.S. Pat. Nos. 5,034,323, 5,231,020, and 5,283,184.

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

A. Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising, et al., *Ann. Rev. Genet.* 22:421–477 (1988). A DNA sequence coding for the desired polypeptide, for example a cDNA sequence encoding the full length NBP46 protein, will preferably be combined with transcriptional and translational initiation regulatory sequences which will direct the transcription of the sequence from the gene in the intended tissues of the transgenic plant, i.e., a root-specific promoter.

Promoters can be identified by analyzing the 5' sequences of a genomic clone in which naturally occurring Nod factor binding protein-specific genes, i.e., NBP46, can be found. At the 5' end of the coding sequence, nucleotide sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions −80 to −100, there is typically a promoter element with a series of adenines surrounding the trinucleotide G (or T) N G. J. Messing, et al., in GENETIC ENGINEERING IN PLANTS, pp. 221–227 (Kosage, Meredith and Hollaender, eds. (1983)).

A number of methods are known to those of skill in the art for identifying and characterizing promoter regions in plant genomic DNA (see, e.g., Jordano, et al., *Plant Cell* 1:855–866 (1989); Bustos, et al., *Plant Cell* 1:839–854 (1989); Green, et al., *EMBO J.* 7:4035–4044 (1988); Meier, et al., *Plant Cell* 3:309–316 (1991); and Zhang, et al., *Plant Physiology* 110:1069–1079 (1996)).

In construction of recombinant expression cassettes of the invention, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens,* and other transcription initiation regions from various plant genes known to those of skill.

Alternatively, the plant promoter may direct expression of the polynucleotide of the instant invention in a specific tissue (tissue-specific promoters) or may be otherwise under more precise environmental control (inducible promoters). Examples of tissue-specific promoters under developmental control include promoters that initiate transcription only in certain tissues, such as roots, fruit, seeds, or flowers. Examples of environmental conditions that may affect transcription by inducible promoters include anaerobic conditions, elevated temperature, or the presence of light.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

B. Production of Transgenic Plants

DNA constructs of the invention may be introduced into the genome of a desired plant host by a variety of conventional techniques. For example, the DNA construct may be introduced directly into the genomic DNA of a plant cell using techniques such as electroporation and microinjection of plant cell protoplasts, or the DNA constructs can be introduced directly into plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski, et al, *EMBO J.* 3:2717–2722 (1984). Electroporation techniques are described in Fromm, et al., *Proc. Nat'l. Acad. Sci. USA* 82:5824 (1985). Ballistic transformation techniques are described in Klein, et al., *Nature* 327:70–73 (1987).

*Agrobacterium tumefaciens*-mediated transformation techniques, including disarming and use of binary vectors, are well described in the scientific literature. See, for example Horsch, et al., *Science* 233:496–498 (1984), and Fraley, et al., *Proc. Nat'l. Acad. Sci. USA* 80:4803 (1983).

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., PROTOPLASTS ISOLATION AND CULTURE, HANDBOOK OF PLANT CELL CULTURE, pp. 124–176, Macmillian Publishing Company, New York (1983); and Binding, REGENERATION OF PLANTS, PLANT PROTOPLASTS, pp. 21–73, CRC Press, Boca Raton (1985). Regeneration can also be obtained from plant callus, explants, organs, or parts thereof. Such regeneration techniques are described generally in Klee, et al., *Ann. Rev. of Plant Phys.* 38:467–486 (1987).

To determine the presence of a reduction or increase of NBP46 activity, a variety of assays can be used including enzymatic, immunochemical, electrophoretic detection assays (either with staining or western blotting), or complex carbohydrate binding assays.

In a preferred embodiment, a competitive solid phase assay is used to measure NBP46 activity (Etzler, M. E., *Glycoconj. J.* 11:395 (1994)). This assay measures the ability of various ligands to inhibit the binding of labeled NBP46 protein to pronase-digested hog gastric mucin blood group A+H substance (HBG A+H) conjugated to Sepharose® (Quinn, J. M. & Etzler, M. E., *Arch. Biochem. Biophys.* 258:535 (1987)).

The nucleic acids of the invention can be used to confer desired traits on essentially any plant. Thus, the invention has use over a broad range of plants, including species from the genera Asparagus, Avena, Brassica, Citrus, Citrullus, Capsicum, Cucurbita, Daucus, Glycine, Hordeum, Lactuca, Lycopersicon, Malus, Manihot, Nicotiana, Oryza, Persea, Pisum, Pyrus, Prunus, Raphanus, Secale, Solanum, Sorghum, Triticum, Vitis, Vigna, and Zea.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Effects of gene manipulation can be observed by northern blots of the mRNA isolated from the tissues of interest. Typically, if the amount of mRNA has increased, it can be assumed that the gene is being expressed at a greater rate than before. Other methods of measuring NBP46 expression would be by measuring the rhizobial infection of the transgenic plants. Alternatively, the ability of the plant to reduce atmospheric nitrogen could be assessed. In addition, levels of NBP46 could be measured immunochemically, i.e., ELISA, RIA, EIA and other antibody based assays well known to those of skill in the art.

V. EXAMPLES

The following examples are offered to illustrate, but not to limit the claimed invention.

Example 1

Characterization and cloning of NBP46

Carbohydrate binding and characterization of NBP46

It has been previously demonstrated that NBP46 is a 46 kDa protein that can be isolated from young *Dolichos biflorus* root extracts by affinity chromatography on hog gastric mucin blood group A+H substance (HBG A+H) conjugated to Sepharose® (Quinn, J. M. & Etzler, M. E., *Arch. Biochem. Biophys.* 258:535 (1987)). The monomeric nature of NBP46 in solution precluded the use of conventional precipitin or agglutination assays in determining the carbohydrate binding specificity of this lectin. Therefore a complex carbohydrate binding assay was employed (Etzler, M. E., *Glycoconj. J.* 11:395 (1994)).

As shown in FIG. 1, various concentrations of blood group substances (A) and oligosaccharides (B) were combined with 109 ng $^{125}$I-NBP46 (isolated as described in Quinn, J. M. & Etzler, M. E., *Arch. Biochem. Biophys.* 258:535 (1987)) and a pronase digest of HBG A+H-Sepharose® (final concentration 1%) in a volume of 100 $\mu$L of 5 mM MOPS, pH 7.2, containing 0.025% Tween-20® and 0.01% $NaN_3$. Hog blood group A+H substance was isolated from hog gastric mucin (Etzler, M. E., *Glyconj. J.* 11:395 (1994)) and de-N-acetylated as described in Etzler, M. E., et al., *Arch. Biochem. Biophys.* 141:588 (1970). After incubation at room temperature overnight, binding was measured as previously described (Etzler, M. E., *Glyconj. J.* 11:395 (1994)). Although the binding of the NBP46 to this resin was inhibited by free HBG A+H (FIG. 1A), no significant inhibition was obtained with up to 50 mM concentrations of any of the monosaccharides present in the blood group substance, including N-acetyl-D-galactosamine and L-fucose, the immunodominant sugars of the blood type A and H determinants, respectively (Watkins, W. M., *Science* 152:172 (1966); and Lloyd, K. O., et al., *Proc. Nat'l. Acad. Sci. USA* 61:1470 (1968)). Individual human ovarian cyst blood group A and H substances (provided by Elvin A. Kabat, Columbia University) were equal to one another in inhibitory capacity but much weaker than HBG A+H (FIG. 1A). De-N-acetylation of the blood type A determinant did not alter the ability of the HBG A+H to inhibit the binding of NBP46 (FIG. 1A).

These results indicated that the binding of NBP46 to the above blood group substances was due to its recognition of some portion of the oligosaccharide chains other than the blood type A and H determinants and that its carbohydrate binding site accommodated more than a simple sugar. The carbohydrate specificity of NBP46 thus differs from the blood type A specific seed lectin from *Dolichos biflorus,* which recognizes the α N-acetyl-D-galactosamine residues which are at the nonreducing ends of the oligosaccharide chains of blood group A substance (Etzler, M. E., et al., *Biochemistry* 9:869 (1970)).

Figure 1B:
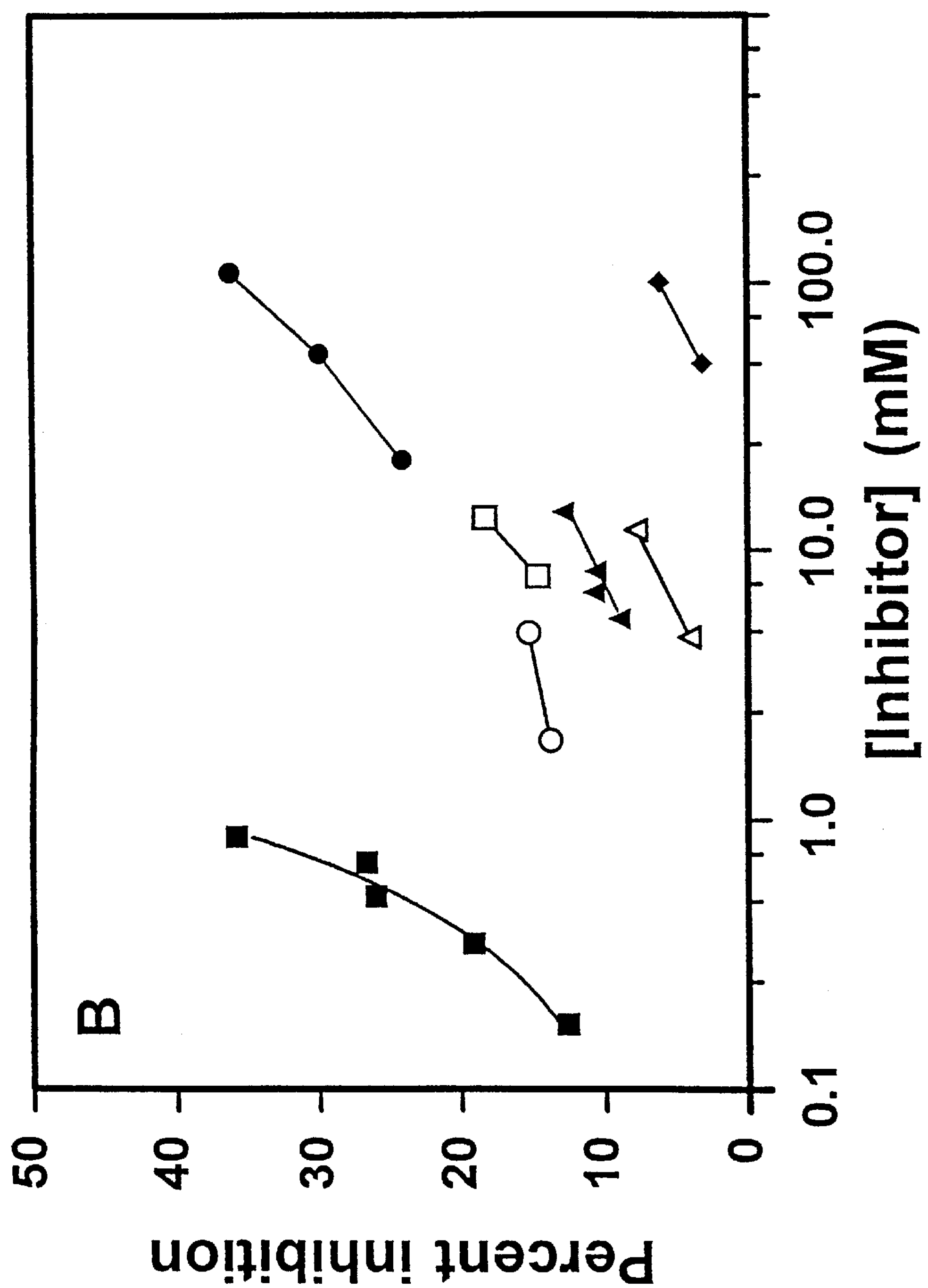

A variety of oligosaccharides were tested in an attempt to obtain more information on the carbohydrate specificity of NBP46 (FIG. 1B). The strongest inhibition was obtained with the purified Nod factor from *Bradyrhizobium japonicum* USDA 110, a bacterial rhizobial strain that nodulates soybean and can also nodulate *Dolichos biflorus.* The Nod factor was isolated as described in Sanjuan, J., et al., *Proc. Nat'l Acad. Sci. USA* 89:8789 (1992). The Nod factor from *Bradyrhizobium japonicum* USDA 110 is composed of a β1–4 N-acetyl-D-glucosamine pentasaccharide backbone, modified by a 2-O-methyl α-L-fucose on C-6 of the sugar at the reducing end and the substitution of the acetyl group on the sugar at the nonreducing end with a $C_{18:1}$ fatty acyl chain (Sanjuan, J., et al., *Proc. Nat'l. Acad. Sci. USA* 89:8789 (1992)). Thus, NBP46 can be characterized as a Nod factor binding lectin.

Phosphohydrolase Activity of NBP46

A search of protein and nucleotide data bases using the NCB1 BLASTP and BLASTN programs (Altschul, S. F., et al., *J. Mol. Biol.* 215:403 (1990)) showed no significant similarities between NBP46 to the amino acid or cDNA sequences of any other plant or animal lectin yet described. It did, however, show 65.6 and 47.6% amino acid identity and 70.7 and 58.7% nucleotide identity with the sequences of a pea nucleotide triphosphatase (Hsieh, H.-L., et al., *Plant Mol. Biol.* 30:135 (1996), GenBank Accession No. Z32743) and an apyrase isolated from potato tubers (Handa, M., et al., *Biochem. Biophys. Res. Comm.* 218:916 (1996)). Thus, the pea triphosphatase gene could also be used in the methods of the invention. Considerably less, but significant, similarity was found with the sequences of several other animal and yeast phosphohydrolases. Of particular interest in this comparison was the presence in all of these sequences of four motifs (designated by the boxes in SEQ ID NO: 2) identified as conserved regions among a variety of plant and animal apyrases (Handa, M., et al., *Biochem. Biophys. Res. Comm.* 218:916 (1996)).

The sequence similarities found between NBP46 and the above enzymes prompted the testing of NBP46 for phosphohydrolase activity. The reactions were conducted in 300 $\mu$L of 60 mM MOPS, pH 6.8, containing 1 mM $MgCl_2$ in a microtiter plate using a multichannel pipette. At various time points up to 4 minutes, 30 or 60 μL aliquots were removed and assayed for inorganic phosphate by a photometric microtiter assay (Drueckes, P., et al., *Anal. Biochem.* 230:173 (1995)). Conditions were chosen so that less than 10% of the total substrate was converted to product, and the initial velocity (v) was determined from the above rate measurements. The $K_m$ of NBP46 for Mg-ADP was found to be 615 μM.

NBP46 catalyzed the hydrolysis of phosphate from both ATP and ADP (FIG. 2) but showed no activity with AMP, pyrophosphate or glucose-6-phosphate. It also had a broad specificity for nucleotide triphosphates, including GTP, CTP and UTP. This substrate specificity has been found to be characteristic of the apyrase category of phosphohydrolases (EC 3.6.1.5). Preincubation of NBP46 with 10 μg/mL of HBG A+H (which results in 46% inhibition of carbohydrate binding activity) resulted in an increase in the $V_{max}$ of NBP46. No increase in phosphatase activity was observed upon preincubation of NBP46 with human blood group H substance at a concentration that shows no inhibition in the carbohydrate binding assay described above (FIG. 2). The $V_{max}$ of NBP46 was also increased in the presence of low concentrations (1 to 5 micromolar) of Nod factors, with lower concentrations required for the Nod factors produced by rhizobia that nodulate the plant than for the *R. meliloti* Nod factor. These results suggest that there is interaction between the carbohydrate binding and phosphatase sites of NBP46.

Isolation and Characterization of NBP46 cDNA and Encoded Protein

Two consensus N-glycosylation sites are present in the sequence of the mature protein at residues 111 and 276. Work in progress in our laboratory has established that NBP46 is indeed glycosylated at at least one of these sites. It should be noted, however, that we do not yet know whether other posttranslational modifications of this protein may occur, such as the COOH-terminal proteolysis that modifies two other lectins from this plant (Etzler, M. E. *Biochemistry* 33:9778–9783 (1994); Schnell, D. T. et al. *Arch. Biochem. Biophys.* 310:229–235 (1994)). A search of protein and nucleotide data bases using the NCB1 TBLASTN and BLASTN programs (Altschul, S. F. et al. *J. Mol. Biol* 215:403–410 (1990)) showed no significant similarities of NBP46 to the amino acid or cDNA sequences of any other plant or animal lectin yet described. It did, however, show 65.6 and 47.6% amino acid identity and 70.7 and 58.7% nucleotide identity with the sequences of a pea nucleotide triphosphatase (Hsieh, H-L. et al. *Plant Mol. Biol.* 30:135–147 (1996)) and an apyrase isolated from potato tubers (Handa, M. and Guidotti, *G. Biochem. Biphys. Res. Comm.* 218: 916–923 (1996)), respectively. Considerably less, but significant, similarity was also found with the sequences of several other animal and yeast phosphohydrolases. Of particular interest in this comparison is the presence in all of these sequences of four motifs (designated by the boxes in SEQ ID NO: 2) identified as conserved regions among a variety of plant and animal apyrases (Handa, M. and Guidotti, *G. Biochem. Biphys. Res. Comm.* 218: 916–923 (1996)).

Figure 2:
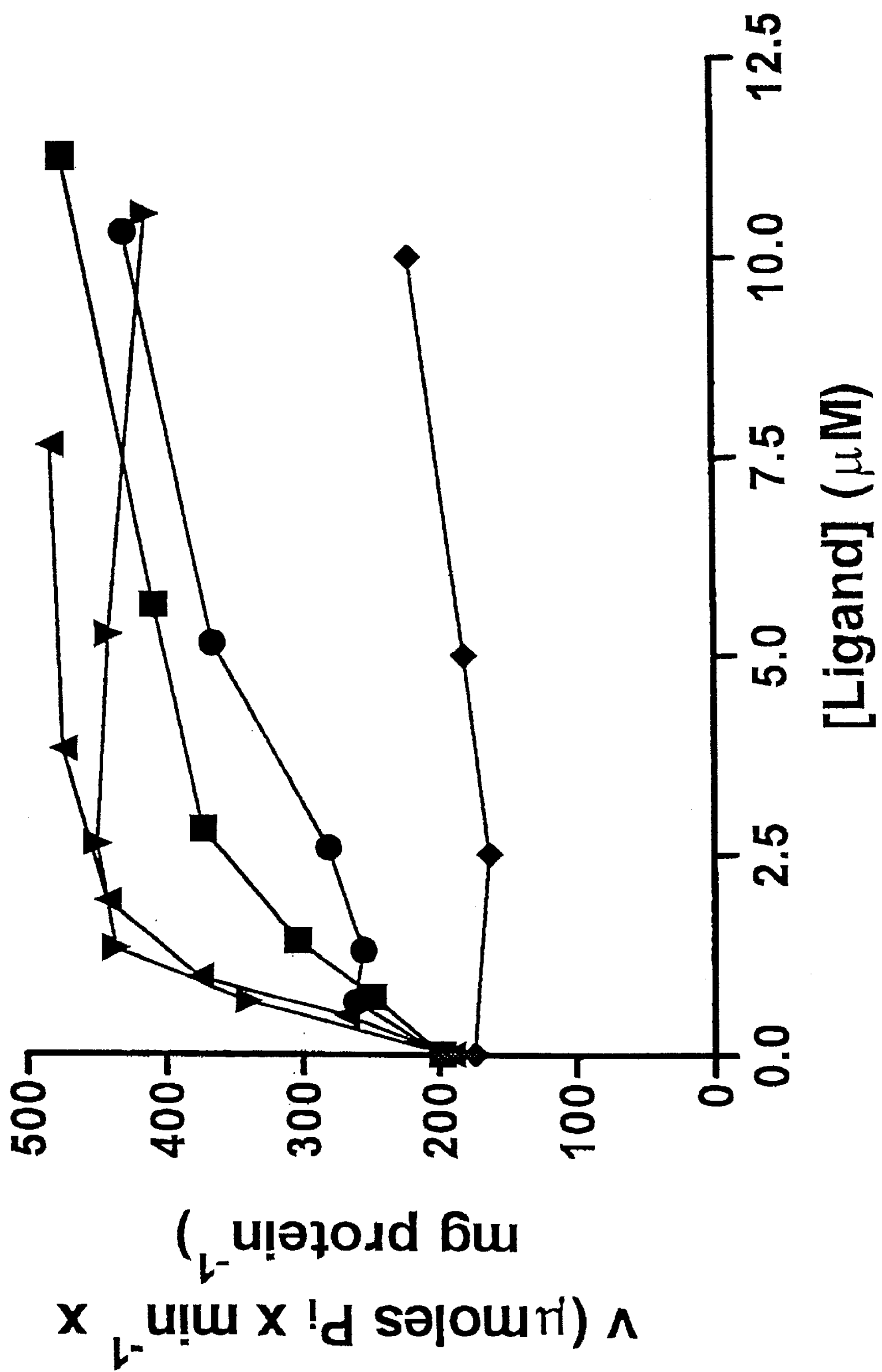
FIG. 2 shows the effect of carbohydrate ligands on phosphatase activity of NBP46, NBP46 (201 ng/ml) was preincubated for 1 hour in the presence of various concentrations of *B. japonicum* USDA110 Nod factor (■), R sp. NGP,234(Ac) Nod factor (▼), R sp. NGR234(S) Nod factor (▲), *R. meliloti* Nod factor (●), or cis-vaccenic acid (♦) and then assayed for phosphatase activity using a final concentration of 3 mM Mg-ADP.

The sequence similarities found among NBP46 and the above enzymes prompted us to test NBP46 for phosphohydrolase activity. NBP46 catalyzes the hydrolysis of phosphate from both ATP and ADP but showed no activity with AMP, pyrophosphate or glucose-6-phosphate. The $K_m$ of NBP46 for $Mg^{++}$-ADP is 615 μM. The lectin has a broad specificity for nucleotide triphosphates, including GTP, CTP and UTP (data not shown). This substrate specificity is characteristic of the apyrase category of phosphohydrolases (EC 3.6.1.5). Preincubation of NBP46 with ligands that are recognized by its carbohydrate binding site results in an increase in the $V_{max}$ of this enzyme. Low micromolar concentrations of the above Nod factors stimulate this increase in activity, with lower concentrations required for the Nod factors produced by rhizobia that modulate the plant than for the *R. meliloti* Nod factor (FIG. 2). Such an increase in enzyme activity is also obtained with low millimolar concentrations of the chitin oligosaccharides and N-acetylglucosamine, but not with N-acetylgalactosamine (data not shown). These results suggest that there is interaction between the carbohydrate binding and phosphatase sites of NBP46. Whether this interaction represents a direct stimulation of the enzyme activity or perhaps a stabilization of the enzyme under the assay conditions remains to be determined.

NBP46 Binds to Chitin and Other Carbohydrates

Figure 3:
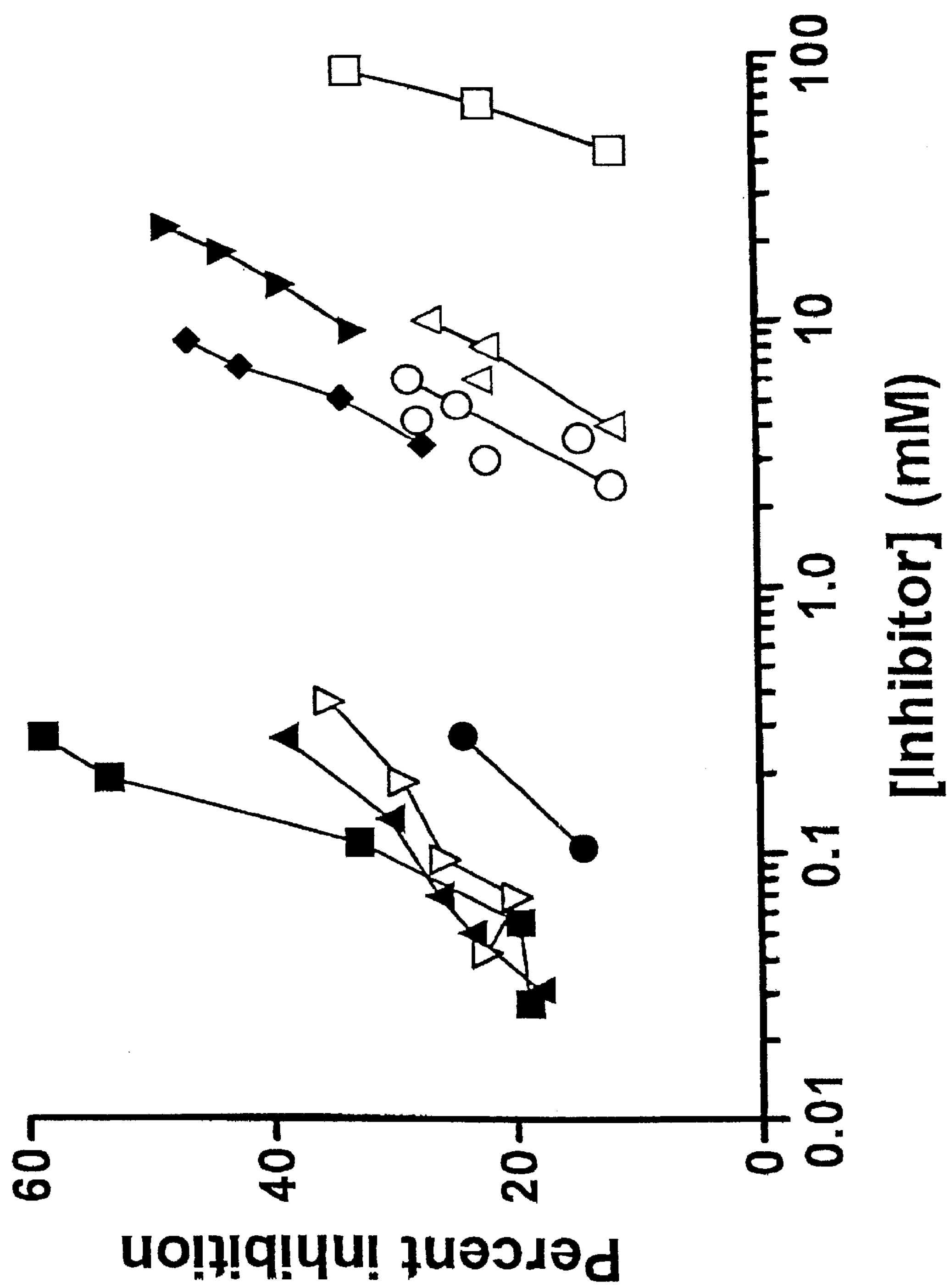
FIG. 3 shows inhibition of binding of $^{125}$I-NBP46 to chitin. Various concentrations of mono- and oligosaccharides were combined with 109 ng $^{125}$I-NBP46 and 250 μg of chitin in a total volume of 100 μl. *B. japonicum* USDA110 Nod factor (■); R. sp. NGR234(NGR$_A$) Nod factor (▲); R. sp. NGR234(NGR$_B$) Nod factor (▽); *R. meliloti* Nod factor (●), N-acetylglucosamine (□), chitin disaccharide (▼); chitin tetrasaccharide (Δ); chitin pentasaccharide (♦), chitin hexasaccharide (O).

NBP46 also binds to chitin, a polymer of β(1–4) linked N-acetyl-D-glucone residues; this binding is saturable with a $B_{max}$ of 28 nmoles of NBP46/gram of chitin and a $K_d$ of 48 nM. Using chitin as a solid phase, a competitive binding assay was utilized to examine the carbohydrate specificity of this protein (FIG. 3). Inhibition of binding was obtained with high concentrations of N-acetyl-D-glocosamine but not with similar concentrations of N-acetyl-D-galactosamine, the C4 epimer of this sugar, nor with other common monosaccharides. The chitin disaccharide gave approximately ten-fold better inhibition than the monosaccharide, whereas the chitin penta- and hexasaccharides were slightly better inhibitors than the disaccharide. No inhibition was obtained with the de-N-acetylated chitin oligosaccharides; however, when tested in the millimolar range of concentrations, several of these oligosaccharides precipitated the lectin even under highly buffered conditions. Whether this precipitation is specific or nonspecific is under investigation.

Of all the oligosaccharides tested, the best inhibition was obtained with the Nod factor isolated from *Bradyrhizobium japonicum* USDA110 (FIG. 3), a rhizobial strain that nodulates *Dolichos biflorus.* The chitolipo-saccharidic Nod factors have been identified as the signals produced by rhizobia that initiate the nodulation of legumes (Denarie, I. et al *Annu. Rev. Biochem.* 65:503–535 (1996)). The *B. japonicum* USDA110 Nod factor consists of a chitin pentasaccharide backbone, modified by a 2-O-methyl α-L-fucose on C-6 of the sugar at the reducing end and the substitution of the acetyl group on the sugar at the nonreducing end with cis-vaccenic acid (Sanjuan, J. et al. *Proc. Natl. Acad. Sci. USA,* 89:8789–8793 (1992); Carlson, R. W. et al. *J. Biol. Chem.* 268:18372-18-81 (1993)). The higher relative affinity of NBP46 for the intact Nod factor than for the chitin pentasaccharide backbone alone indicates that the modifications of this backbone contribute to the recognition of the Nod factor by the lectin. No significant inhibition of NBP46 binding to chitin was obtained with cis-vaccenic acid when tested at concentrations up to 1.2 mM nor with L-fucose at concentrations up to 50 mM.

Two Nod factors from Rhizobium sp. NGR234, another strain that nodulates *Dolichos biflorus,* were also able to inhibit the binding of NBP46 to chitin. These Nod factors differ from the USDA110 10 Nod factor in that they have a sulfate on C-3 ($NodNGR_A$) or an acetate on C-4 ($NodNGR_B$) of the 2-O-methylfucose; they are also methylated on the amino group and partially carbamoylated at C-3, C-4 or C-6 of the sugar at the nonreducing end (Price, N. P. J. et al. *Carbohyd. Res.* 289:115–136 (1993)). The Nod factor from *Rhizobium meliloti,* a strain that does not modulate Dolichos biflorus, gave the weakest inhibition when tested at equivalent concentrations (FIG. 3). This Nod factor differs from the USDA110 Nod factor in that it has a chitin tetrasaccharide backbone, contains a sulfate instead of a fucose at the reducing end and is acetylated at C-6 of the sugar at the nonreducing end (Lerouge, P. *Nature* 344:781–784 (1990)).

Although the differences in relative affinity of NBP46 for the above Nod factors indicate a small preference of the lectin for Nod factors produced by rhizobia that modulate the plant, it must be pointed out that both the *B. japonicum* USDA110 and R. sp. NGR234 strains are only weak nodulators of *Dolichos fiblorus,* and the nodules formed with the former strain do not fix nitrogen. Nod factors from rhizobial strains that are strong nodulators of this plant have not yet been purified or characterized.

Antiserum Raised Against NBP46 Inhibits Nodulation

Confocal immunofluorescence microscopy of whole mounts of 7-day old *Dolichos biflorus* roots that had been fixed prior to staining showed that NBP46 is present on the surfaces of the newly emerging and young root hairs. Treatment of young roots of this plant with antiserum to the lectin inhibited the ability of these roots to be nodulated by rhizobia (Table 1). Although it is possible that such inhibition could be due to stearic hindrance of adjacent sites, these results, coupled with the above finding that NBP46 is a Nod factor binding protein, suggest that this root lectin may play a role in rhizobium-legume symbiosis either as a host/strain specific receptor or perhaps as a second, less stringent receptor postulated for this process (Ardourel, M. et al. *Plant Cell* 6:1357–1374 (1994)). Previous attempts to implicate lectins in this symbiosis have been focused on the legume seed lectins (Diaz, C. L. et al. *Nature* 338:579–581 (1989); Hirsch, A. M. et al. *Symbiosis* 19:155–173 (1995)), which have not been reported to bind Nod factors. It is also possible that NBP46 may function in the recognition of endogenous Nod-factor like signals that have been proposed to play a role in the regulation of plant growth and organogenesis (Etzler, M. E. *Biochemistry* 33:9778–9783 (1994)).

TABLE 1

Effect of anti-NBP46-serum on nodulation of *D. biflorus* roots

| Treatment | Average number of nodules (± S.E.) Treated region of root | Region of root emerged after treatment |
|---|---|---|
| Untreated | 3.6 ± 0.5 | 2.2 ± 0.2 |
| Preimmunization serum | 3.4 ± 0.5 | 1.6 ± 0.2 |
| Anti-NBP46-serum | 0.6 ± 0.2 | 1.4 ± 0.2 |

The roots of 2 sets of 10 3-day old *Dolichos biflorus* plants were immersed for 1 hour in 1/100 dilutions of preimmunization serum or anti-NBP46-serum, washed and transferred to growth pouches. A third set of 10 pts was put directly in growth pouches. Half of each set of plants was inoculated with Bradyrhizobium sp. 24A10. After 3 weeks the number of nodules in the treated region as well as in the region of root that emerged after treatment were recorded. No nodules were observed on the roots that had not been inoculated with rhizobia.

DISCUSSION

The low concentrations ($10^{-12}$ of Nod factor that have been found to induce physiological responses in legumes (Denarie, I. et al *Annu. Rev. Biochem.* 65:503–535 (1996)) predict that Nod factor receptors have high affinity for their ligands. Indeed, high affinity binding sites for Nod factors have been found on particulate fractions from roots of the legume, *Medicago truncatula* (Niebel, A. *Mol. Plant-Microbe Interact.* 10:132–134 (1997)). Although the inhibition data show the relative affinities of NBP46 for its ligands, they do not enable the determination of the absolute affinities of this lectin for the Nod factors. The concentrations of Nod factors required for the stimulation of increased phosphatase activity suggest that the $K_{d's}$ may be in the high nanomolar to low micromolar range. It should be noted, however, that NBP46 is primarily a monomer in solution (Quinn, J. M. and Etzler, M. E. *Arch. Biochem. Biophys.* 258:535–544 (1987)); as established with antibodies (Hornick, C. L. and Karush, F. *Immunochem.* 9:325–340 (1972)), the multivalence that would occur when this lectin is associated with the cell surface would increase its apparent affinity for multivalent ligands such as Nod factor micelles or Nod factor on the surface of rhizobia by several orders of magnitude.

The presence of both carbohydrate binding activity and apyrase activity on NBP46 and the apparent interaction of these sites suggest that, upon binding its carbohydrate ligand, NBP46 may play a role in activating downstream events either directly by signal transduction or indirectly, perhaps by serving as a motor for transport of the carbohydrate. In this context, it is of interest that the human CD39 lymphoid cell activation antigen, one of the apyrases found to have some sequence similarity to NBP46, is thought to be involved in the regulation of B cell adhesion (Kansas, G. S. et al. *J. Immunol.* 146:2235–2244 (1991)). Although these other apyrases have not been tested for lectin activity, it is possible that such dual activities of these proteins may have been conserved throughout evolution.

The unique amino acid sequence, carbohydrate specificity and apyrase activity of NBP46 distinguish this lectin from the conventional lectins found in abundance in the seeds of legumes (Sharon, N. and Lis, H. *FASEB J.* 4:3198–3208 (1990)). The possibility that other such plant lectin/enzymes exist is suggested by the recent finding of a CDNA from *Arabidopsis thaliana* that encodes a receptor-like serine/threonine kinase as well as a legume seed lectin-like domain (Herve, C. et al. *J. Mol. Biol* 258:778–788 (1996)). NBP46 may thus be on one of many multifunctional carbohydrate binding proteins that may function in plant oligosaccharide signaling events. A variety of transgenic experiments are underway to elaborate its role in such processes.

METHODS

Preparation of NBP46.

NBP46 was extracted from the roots of 7-day old *Dolichos biflorus* plants and isolated by affinity chromatography on hog blood group A+H–Sepharose as previously described (Quinn, J. M. and Etzler, M. E. *Arch. Biochem. Biophys.* 258:535–544 (1987)), followed by ion exchange chromatography. It was iodinated using the iodine monochloride procedure as previously described (Etzler, M. E. *Glycoconj. J.* 11:395–399 (1994)), which gave a specific activity of approximately $500\times10^6$ cpm/mg protein.

Carbohydrate binding assays.

Solid phase binding assays were conducted using iodinated NBP46 and purified shrimp chitin powder (Sigma Chemical Company, St. Louis, Mo.), which was N-acetylated prior to use with 15 mM acetic anhydride in 0.5 M $NaHCO_3$ for one hour at room temperature. The assays were conducted in a final volume of 100 $\mu$l of 10 mM MOPS buffer, pH 7.2, containing 0.02% Tween-20 and 0.01% $NaN_3$. After incubation at room temperature for two hours, binding was measured as previously described (Etzler, M. E. *Glycoconj. J.* 11:395–399 (1994)).

*Bradyrhizobium japonicum* USDA110 Nod factor was isolated as previously described (Sanjuan, J. et al. *Proc. Natl. Acad. Sci. USA,* 89:8789–8793 (1992)). The Nod factors from *Rhizobium meliloti* and Rhizobium sp. NGR234 were graciously provided by Dr. Jean Denarie, CNRS-INRA, Toulouse, France. Monosaccharides and the chitin disaccharide were purchased from Sigma Chemical Co., St. Louis, Mo., the other chitin oligosaccharides were obtained from Seikagaku Corp., Tokyo, Japan.

Cloning of NBP46 cDNA.

Total RNA was isolated (Taylor, B. and Powell, A. *Focus* 4:4–6 (1982)) from the roots of 1-day-old *D. biflorus* plants and reverse transcribed using M-NMV reverse transcriptase and random hexanucleotide primers (Tabor S. RNA-dependent DNA polymerases. In *Current Protocols in Molecular Biology,* F. M. Ausubel, F. M., et al., Eds., John Wiley & Sons, Inc., Vol. 1, pp. 3.7.1–3.7.3 (1987)). This cDNA was used as a template in a PCR reaction employing Taq polymerase and degenerate sense and antisense primers corresponding to amino acids 6–12 and 244–249 in SEQ ID NO:2. The PCR was performed in an automated thermal cycler for 35 cycles of 94° C. for 2 min, 37° C. for 2 min, and 72° C. for 2 min. The predominant 727 bp fragment was isolated on a 1.2% agarose gel, cloned into the pCRII vector (InVitrogen) and sequenced (Sanger, F. et al. *Proc. Natl. Acad. Sci. USA* 74:5463–5467 (1977)). Gene specific primers were used in 5' and 3' RACE reactions (Frohman, M. A. *Proc. Natl. Acad. Sci USA* 85:8998–9002 (1988)); the products were cloned into the pCRII vector and sequenced. The full length (1527 bp) cDNA was assembled by ligating the two RACE products together using an int Sac1 site. The sequences of the overlapping regions of the 5' and 3' RACE products and the original PCR fragment were identical.

Phosphatase assays.

N-BP46 (201 ng/ml) was incubated at 25° C. in the presence of various concentrations of substrate in a final volume of 100 μl of 60 mM MOPS, pH 6.8, containing 1 mM $MgCl_2$. The reactions were conducted in a microtiter plate using a multichannel pipette. At various time points, 30 μl aliquots were removed and assayed for inorganic phosphate by a photometric microtiter assay (Drueckes, P. et al. *Anal. Biochem.* 230:173 (1995)), modified by using four parts ammonium molybdate reagent to one part 10% ascorbate for the reagent mixture. Conditions were chosen so that less than 10% of the total substrate was converted to product.

Immunofluorescence microscopy.

Roots from 7-day old *Dolichos biflorus* plants were fixed for 45 minutes at 4° C. in 0.01 M phosphate buffer, pH 7.2, containing 0, 15 M NaCl and 0.3% paraformaldehyde. After washing, the roots were treated for 20 minutes with a 1/250 dilution of preimmunization serum or antiserum prepared against recombinant NBP46. After washing, the roots were treated for 20 minutes with fluorescein-labeled goat anti-rabbit IgG (Sigma Chemical Co., St. Louis, Mo.), washed and examined with a Leica TCS NT confocal microscope using a 488 nm laser excitation line and a 560 barrier filter. Confocal images were reconstructed with Imagespace software.

Nodulation.

*Dolichos biflorus* seeds were sterilized by shaking for 15 minutes in 70% ethanol, followed by 15 minutes in 3% hydrogen peroxide. After extensive washing with sterile $H_2O$, the seeds were germinated and grown in sterile growth pouches. At 3 days, the roots were inoculated with 100 μl of B. sp. 24A10 ($1\times10^7$ cells/ml). The number of nodules per root was determined after 3 weeks. Antiserum and preimmunization serum used to treat the roots were sterilized by filtration through a 0.45 μm filter.

Example 2

Isolation of NBP46 from Other Species

NBP46 nucleic acids have also been isolated from *Medicago sativa* (SEQ ID NO:8 and 9–12) and *Lotus japonicus* (SEQ ID NO:13 and 14–17). These nucleic acids were obtained by RT-PCR as follows. Messenger RNA was obtained form the roots of both species and reverse transcribed using oligo-dT primers. Degenerate PCR primers were designed to conserved sequences of the *D. biflorus* NBP46 disclosed here and the *Pisum sativa* nucleotide triphosphatase gene described by Hsieh, H.-L., et at., *Plant Mol. Biol.* 30:135(1996). These were used to generate internal 850 bp fragments from both *Medicago sativa* and *Lotus japonicus.* cDNA species-specific primers then designed for both 5' and 3' RACE. Full length clones were obtained using primers designed to the 5' and 3' ends of the RACE products. Duplicate clones from each species were obtained in separate PCR reactions and sequenced in their entirety in both directions.

Example 3

Isolation of DBX from *D. biflorus*

A second gene also involved in oligosaccharide signaling has been isolated from *D. Biflorus* (SEQ ID NO:18 and 19).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A transgenic plant with enhanced rhizobial binding to roots of the plant comprising an expression cassette containing a plant promoter operably linked to a heterologous NBP46 polynucleotide that specifically hybridizes to SEQ ID NO:1 under hybridization conditions that include at least one wash in 0.2× SSC at a temperature of at least about 60° C. for 20 minutes and that encodes an NBP46 polypeptide that enhances rhizobial binding to roots of the plant.

2. The transgenic plant of claim 1, wherein the NBP46 polypeptide is SEQ ID NO:2.

3. The transgenic plant of claim 1, which is not a legume.

4. A method of enhancing rhizobial binding to roots of a plant, the method comprising introducing into the plant an expression cassette comprising plant promoter operably linked to a heterologous NBP46 polynucleotide that specifically hybridizes to SEQ ID NO:1 under hybridization conditions that include at least one wash in 2.0× SSC at a temperature of at least 60° C. for 20 minutes and that encodes an NBP46 polypeptide that enhances rhizobial binding to roots of the plant.

5. The method of claim 4, wherein the heterologous NBP46 polynucleotide is SEQ ID NO:1.

6. The method of claim 2, wherein the NBP46 polypeptide has the amino acid sequence as shown in SEQ ID NO:2.

7. The method of claim 4, wherein the plant is not a legume.

8. The method of claim 4, wherein the expression cassette is introduced into the plant through a sexual cross.

9. An isolated nucleic acid molecule comprising a sequence encoding an NBP 46 polypeptide that is at least about 80% identical to SEQ ID NO:9 and that enhances rhizobial binding to roots of a transgenic plant comprising the sequence.

10. The isolated nucleic acid molecule of claim 9, wherein the sequence encoding an NBP 46 polypeptide is SEQ ID NO:8.

11. A transgenic plant comprising an expression cassette comprising a nucleic acid encoding an NBP 46 polypeptide that is at least about 80% identical to SEQ ID NO:9 and that enhances rhizobial binding to roots of a transgenic plant comprising the nucleic acid, wherein the nucleic acid is operably linked to a heterologous promoter sequence.

12. A method enhancing rhizobial binding to roots of a plant, the method comprising introducing into the plant an expression cassette comprising a nucleic acid encoding an NBP 46 polypeptide that is at least about 80% identical to SEQ ID NO:9 and that enhances rhizobial binding to roots of a transgenic plant comprising the sequence, wherein the nucleic acid is operably linked to a heterologous promoter sequence.

13. The method of claim 12, wherein the NBP 46 polypeptide enhances phosphohydrolase activity.

14. An isolated nucleic acid molecule comprising a sequence encoding an NBP 46 polypeptide that is at least about 80% identical to SEQ ID NO:15 and that enhances rhizobial binding to roots of a transgenic plant comprising the sequence.

15. The isolated nucleic acid molecule of claim 14, wherein the sequence encoding an NB46 polypeptide is SEQ ID NO:13.

16. A transgenic plant comprising an expression cassette comprising a nucleic acid encoding an NBP 46 polypeptide that is at least about 80% identical to SEQ ID NO:15 and that enhances rhizobial binding to roots of a transgenic plant comprising the nucleic acid, wherein the nucleic acid is operably linked to a heterologous promoter sequence.

17. A method enhancing rhizobial binding to roots of a plant, the method comprising introducing into the plant an expression cassette comprising a nucleic acid encoding an NBP 46 polypeptide that is at least about 80% identical to SEQ ID NO:15 and that enhances rhizobial binding to roots of a transgenic plant comprising the nucleic acid, wherein the nucleic acid is operably linked to a heterologous promoter sequence.

18. The method of claim 17, wherein the NBP 46 polypeptide enhances phosphohydrolase activity.

19. An isolated nucleic acid molecule comprising a sequence encoding an NBP 46 polypeptide that is at least about 80% identical to SEQ ID NO:2 and that enhances rhizobial binding to roots of a transgenic plant comprising the sequence.

20. The isolated nucleic acid molecule of claim 19, wherein the sequence encoding an NBP 46 polypeptide is SEQ ID NO:1.

21. A transgenic plant comprising an expression cassette comprising a nucleic acid encoding an NBP46 polypeptide that is at least 80% identical to SEQ ID NO:2 and that enhances rhizobial binding to roots of a transgenic plant comprising the nucleic acid.

* * * * *

SEQUENCE LISTING

```
<160> NUMBER OF SEQ ID NOS: 19

<210> SEQ ID NO 1
<211> LENGTH: 1643
<212> TYPE: DNA
<213> ORGANISM: Dolichos biflorus
<220> FEATURE:
<221> NAME/KEY: CDS
<222> LOCATION: (51)..(1439)
<223> OTHER INFORMATION: NBP46 (DB46) Nod factor binding lectin
```

-continued

```
<221> NAME/KEY: mat_peptide
<222> LOCATION: (195)..(1436)

<400> SEQUENCE: 1

gaaactgaaa cgagtactct ttcagtggtg aggttctgag agattcagaa atg aat      56
                                                          Met Asn

tgg gtg tgg cca aag aca aag agc atg agc ttc cta ctc ctc atc act       104
Trp Val Trp Pro Lys Thr Lys Ser Met Ser Phe Leu Leu Leu Ile Thr
    -45                 -40                 -35

ttt cta ctc ttc tca ttg cca aaa ctt tct tct tcg caa tat gtt ggg       152
Phe Leu Leu Phe Ser Leu Pro Lys Leu Ser Ser Ser Gln Tyr Val Gly
-30                 -25                 -20                 -15

aac agt atc tta cta aat cat cgt aag ata ctt ccc aac cag gaa ctc       200
Asn Ser Ile Leu Leu Asn His Arg Lys Ile Leu Pro Asn Gln Glu Leu
                -10                  -5              -1   1

ctt acc tct tac gct gtc atc ttt gat gct ggt agc tct ggg agt cgt       248
Leu Thr Ser Tyr Ala Val Ile Phe Asp Ala Gly Ser Ser Gly Ser Arg
          5                  10                  15

gtc cat gtc ttc aat ttt gac cag aac tta gat ctc ctg cac att ggc       296
Val His Val Phe Asn Phe Asp Gln Asn Leu Asp Leu Leu His Ile Gly
     20                  25                  30

aat gac ctc gag ttt aca aaa aag atc aaa ccc ggt ttg agc tca tac       344
Asn Asp Leu Glu Phe Thr Lys Lys Ile Lys Pro Gly Leu Ser Ser Tyr
 35                  40                  45                  50

gct gat aag cct gaa aaa gct gca gaa tct ctc att cca ctt ttg gag       392
Ala Asp Lys Pro Glu Lys Ala Ala Glu Ser Leu Ile Pro Leu Leu Glu
                 55                  60                  65

gaa gct gaa gat gtt gtc cct gag gaa ctg cac ccc aag aca ccc ctt       440
Glu Ala Glu Asp Val Val Pro Glu Glu Leu His Pro Lys Thr Pro Leu
             70                  75                  80

aag ctt ggg gca aca gca ggt ttg agg ctc ttg gat ggg gat gct gct       488
Lys Leu Gly Ala Thr Ala Gly Leu Arg Leu Leu Asp Gly Asp Ala Ala
         85                  90                  95

gaa aag ata ttg caa gcg gtt agg gaa atg ttc agg aac aga agt tcc       536
Glu Lys Ile Leu Gln Ala Val Arg Glu Met Phe Arg Asn Arg Ser Ser
    100                 105                 110

ctg agc gtt caa cct gat gca gta tct gtt att gat gga acc caa gaa       584
Leu Ser Val Gln Pro Asp Ala Val Ser Val Ile Asp Gly Thr Gln Glu
115                 120                 125                 130

ggt tct tac tta tgg gtt aca gtt aac tat ctg tta gga aag ttg gga       632
Gly Ser Tyr Leu Trp Val Thr Val Asn Tyr Leu Leu Gly Lys Leu Gly
                135                 140                 145

aag aag ttt aca aaa act gtg gga gtg ata gat ctt gga ggt gct tca       680
Lys Lys Phe Thr Lys Thr Val Gly Val Ile Asp Leu Gly Gly Ala Ser
            150                 155                 160

gtt caa atg gct tat gct gtc tca aga aat aca gct aaa aat gcc cca       728
Val Gln Met Ala Tyr Ala Val Ser Arg Asn Thr Ala Lys Asn Ala Pro
        165                 170                 175

aaa cca cca caa gga gag gat cca tac atg aag aag ctt gta ctc aag       776
Lys Pro Pro Gln Gly Glu Asp Pro Tyr Met Lys Lys Leu Val Leu Lys
    180                 185                 190

gga aag aaa tat gac ctt tat gtt cac agt tac ttg cgt tat ggt aac       824
Gly Lys Lys Tyr Asp Leu Tyr Val His Ser Tyr Leu Arg Tyr Gly Asn
195                 200                 205                 210

gac gca gca cgt gtt aag att ttt aag acc act gat ggt gct gct agt       872
Asp Ala Ala Arg Val Lys Ile Phe Lys Thr Thr Asp Gly Ala Ala Ser
                215                 220                 225

cct tgt cta ttg gca ggc tat gaa gat ata tac aga tat tcc gga gaa       920
Pro Cys Leu Leu Ala Gly Tyr Glu Asp Ile Tyr Arg Tyr Ser Gly Glu
            230                 235                 240
```

-continued

```
tcg tac aat atc tat ggt ccc act tct ggt gcc aac ttt aat gag tgc      968
Ser Tyr Asn Ile Tyr Gly Pro Thr Ser Gly Ala Asn Phe Asn Glu Cys
        245                 250                 255

cgt gac cta gct ctt cag att ctc aga ttg aat gag cca tgt tcc cat     1016
Arg Asp Leu Ala Leu Gln Ile Leu Arg Leu Asn Glu Pro Cys Ser His
    260                 265                 270

gaa aac tgc acc ttt ggt ggg ata tgg gat ggt gga aaa gga agt gga     1064
Glu Asn Cys Thr Phe Gly Gly Ile Trp Asp Gly Gly Lys Gly Ser Gly
275                 280                 285                 290

cag aaa aac ctt gtt gtt act tca gct ttc tac tat agg tct tct gag     1112
Gln Lys Asn Leu Val Val Thr Ser Ala Phe Tyr Tyr Arg Ser Ser Glu
                295                 300                 305

gtt ggt ttt gtc act cct ccc aat tcc aaa aat cgc cct ctg gat ttt     1160
Val Gly Phe Val Thr Pro Pro Asn Ser Lys Asn Arg Pro Leu Asp Phe
            310                 315                 320

gaa act gca gct aaa caa gct tgt agt tta aca ttc gag gaa gcg aaa     1208
Glu Thr Ala Ala Lys Gln Ala Cys Ser Leu Thr Phe Glu Glu Ala Lys
        325                 330                 335

tcc act ttt cca aat gtt gag aaa gat aaa ctt cca ttt gta tgc gtg     1256
Ser Thr Phe Pro Asn Val Glu Lys Asp Lys Leu Pro Phe Val Cys Val
    340                 345                 350

gat ttc aca tac cag tat aca ttg ctt gtt gat gga ttt ggc cta gat     1304
Asp Phe Thr Tyr Gln Tyr Thr Leu Leu Val Asp Gly Phe Gly Leu Asp
355                 360                 365                 370

cca gag caa gag att aca gtg gca gaa gga att gaa tat caa gat gcc     1352
Pro Glu Gln Glu Ile Thr Val Ala Glu Gly Ile Glu Tyr Gln Asp Ala
                375                 380                 385

att gtg gaa aca gca tgg cct cta gga act gcc ata gaa gcc ata tca     1400
Ile Val Glu Thr Ala Trp Pro Leu Gly Thr Ala Ile Glu Ala Ile Ser
            390                 395                 400

tct ttg cct aaa ttt aat cgt cta atg tat ttt atc taa gccatgtcct      1449
Ser Leu Pro Lys Phe Asn Arg Leu Met Tyr Phe Ile
        405                 410                 415

ccacttatga ccactttaat taaaataaaa ctcacccttt tcactaaaaa aaaaaaaaaa   1509

aaaagtcctt ttttattcca ttgagtatca agtgttaatt tgtttctgac aaatggaggt   1569

gtaaaagtga aacaaagtat gtttttgtca gatacgaatg gaagtagggt tatgatgaaa   1629

aaaaaaaaaa aaaa                                                      1643


<210> SEQ ID NO 2
<211> LENGTH: 462
<212> TYPE: PRT
<213> ORGANISM: Dolichos biflorus
<220> FEATURE:
<221> NAME/KEY: PEPTIDE
<222> LOCATION: (52)..(73)
<223> OTHER INFORMATION: motif identified as conserved region among a
      variety of plant and animal apyrases
<221> NAME/KEY: PEPTIDE
<222> LOCATION: (128)..(144)
<223> OTHER INFORMATION: motif identified as conserved region among a
      variety of plant and animal apyrases
<221> NAME/KEY: PEPTIDE
<222> LOCATION: (173)..(195)
<223> OTHER INFORMATION: motif identified as conserved region among a
      variety of plant and animal apyrases
<221> NAME/KEY: PEPTIDE
<222> LOCATION: (200)..(220)
<223> OTHER INFORMATION: motif identified as conserved region among a
      variety of plant and animal apyrases

<400> SEQUENCE: 2

Met Asn Trp Val Trp Pro Lys Thr Lys Ser Met Ser Phe Leu Leu Leu
```

-continued

```
1               5                   10                  15

Ile Thr Phe Leu Leu Phe Ser Leu Pro Lys Leu Ser Ser Ser Gln Tyr
            20                  25                  30

Val Gly Asn Ser Ile Leu Leu Asn His Arg Lys Ile Leu Pro Asn Gln
        35                  40                  45

Glu Leu Leu Thr Ser Tyr Ala Val Ile Phe Asp Ala Gly Ser Ser Gly
    50                  55                  60

Ser Arg Val His Val Phe Asn Phe Asp Gln Asn Leu Asp Leu Leu His
65                  70                  75                  80

Ile Gly Asn Asp Leu Glu Phe Thr Lys Lys Ile Lys Pro Gly Leu Ser
                85                  90                  95

Ser Tyr Ala Asp Lys Pro Glu Lys Ala Ala Glu Ser Leu Ile Pro Leu
            100                 105                 110

Leu Glu Glu Ala Glu Asp Val Val Pro Glu Glu Leu His Pro Lys Thr
        115                 120                 125

Pro Leu Lys Leu Gly Ala Thr Ala Gly Leu Arg Leu Leu Asp Gly Asp
    130                 135                 140

Ala Ala Glu Lys Ile Leu Gln Ala Val Arg Glu Met Phe Arg Asn Arg
145                 150                 155                 160

Ser Ser Leu Ser Val Gln Pro Asp Ala Val Ser Val Ile Asp Gly Thr
                165                 170                 175

Gln Glu Gly Ser Tyr Leu Trp Val Thr Val Asn Tyr Leu Leu Gly Lys
            180                 185                 190

Leu Gly Lys Lys Phe Thr Lys Thr Val Gly Val Ile Asp Leu Gly Gly
        195                 200                 205

Ala Ser Val Gln Met Ala Tyr Ala Val Ser Arg Asn Thr Ala Lys Asn
    210                 215                 220

Ala Pro Lys Pro Pro Gln Gly Glu Asp Pro Tyr Met Lys Lys Leu Val
225                 230                 235                 240

Leu Lys Gly Lys Lys Tyr Asp Leu Tyr Val His Ser Tyr Leu Arg Tyr
                245                 250                 255

Gly Asn Asp Ala Ala Arg Val Lys Ile Phe Lys Thr Thr Asp Gly Ala
            260                 265                 270

Ala Ser Pro Cys Leu Leu Ala Gly Tyr Glu Asp Ile Tyr Arg Tyr Ser
        275                 280                 285

Gly Glu Ser Tyr Asn Ile Tyr Gly Pro Thr Ser Gly Ala Asn Phe Asn
    290                 295                 300

Glu Cys Arg Asp Leu Ala Leu Gln Ile Leu Arg Leu Asn Glu Pro Cys
305                 310                 315                 320

Ser His Glu Asn Cys Thr Phe Gly Gly Ile Trp Asp Gly Gly Lys Gly
                325                 330                 335

Ser Gly Gln Lys Asn Leu Val Val Thr Ser Ala Phe Tyr Tyr Arg Ser
            340                 345                 350

Ser Glu Val Gly Phe Val Thr Pro Pro Asn Ser Lys Asn Arg Pro Leu
        355                 360                 365

Asp Phe Glu Thr Ala Ala Lys Gln Ala Cys Ser Leu Thr Phe Glu Glu
    370                 375                 380

Ala Lys Ser Thr Phe Pro Asn Val Glu Lys Asp Lys Leu Pro Phe Val
385                 390                 395                 400

Cys Val Asp Phe Thr Tyr Gln Tyr Thr Leu Leu Val Asp Gly Phe Gly
                405                 410                 415

Leu Asp Pro Glu Gln Glu Ile Thr Val Ala Glu Gly Ile Glu Tyr Gln
            420                 425                 430
```

-continued

```
Asp Ala Ile Val Glu Thr Ala Trp Pro Leu Gly Thr Ala Ile Glu Ala
        435                 440                 445

Ile Ser Ser Leu Pro Lys Phe Asn Arg Leu Met Tyr Phe Ile
    450                 455                 460


<210> SEQ ID NO 3
<211> LENGTH: 6265
<212> TYPE: DNA
<213> ORGANISM: Dolichos biflorus
<220> FEATURE:
<223> OTHER INFORMATION: genomic sequence of NBP46 (DB46)
<221> NAME/KEY: exon
<222> LOCATION: (633)..(944)
<221> NAME/KEY: intron
<222> LOCATION: (945)..(1022)
<221> NAME/KEY: exon
<222> LOCATION: (1023)..(1151)
<221> NAME/KEY: intron
<222> LOCATION: (1152)..(1559)
<221> NAME/KEY: exon
<222> LOCATION: (1560)..(1616)
<221> NAME/KEY: intron
<222> LOCATION: (1617)..(1697)
<221> NAME/KEY: exon
<222> LOCATION: (1698)..(1790)

<400> SEQUENCE: 3

ctagatgtga agtgatttta atcttgcaac tggtgtaaat aaatcataat acaatatctt     60

atcttaaaaa taaaatcttc ataaaaaata aatataatga ttaaattatc ataaataaat    120

aagtaattat ttccttacct aacatgatgg ccagctcata taataacatc gcttcttgga    180

gcatatcaat gacgaaaacg tggacgcaaa ttattggcct cggggatctg ctttctgcaa    240

atacttgttt ctcccgagaa ccggattctc attaatttct agttgttctc gtaaattgct    300

cactttattt tcattgtaaa gtaaaaataa ttttctacta aaaacgatat tcaccatgtt    360

agtcacatac acattcaata atatttaaaa tgttatttat ttaatgggaa gaagatttaa    420

taattggggt tagttcttac aataatacat actcaacaaa atttttcctc aaatatcaca    480

cgatagtaat atattaatct aatataatct cacaaaatca tctccatatt tatatatttc    540

atatagatga tgttatcatg gacgtggatc tctgcgacca tagcatttta catctatata    600

tagtggcaag agtgacgatt agtgcaaact gaaacgagta ctctttcagt ggtgaggttc    660

tgagagattc agaaatgaat tgggtgtggc caaagacaaa gagcatgagc ttcctactcc    720

tcatcacttt tctactcttc tcattgccaa aactttcttc ttcgcaatat gttgggaaca    780

gtatcttact aaatcatcgt aagatacttc ccaaccagga actccttacc tcttacgctg    840

tcatctttga tgctggtagc tctgggagtc gtgtccatgt cttcaatttt gaccagaact    900

tagatctcct gcacattggc aatgacctcg agtttacaaa aaaggtcaaa ctgaaacctt    960

aaattattca ttattatttt cttcatctta ctcttacatt cttcttcatt attctggtgc   1020

agatcaaacc cggtttgagc tcatacgctg ataagcctga aaaagctgca gaatctctca   1080

ttccactttt ggaggaagct gaagatgttg tccctgagga actgcacccc aagacacccc   1140

ttaagcttgg ggtgagtatt tctcatctct acttttgcca cagattaata tgtcacactt   1200

ttacatgaaa catgattaag ttctttaaac atgttgatta aagggtgaca gtttgtattt   1260

tttaatcaag taatctagaa cttaaactat ggtaataata taaaatgaat atgaaactaa   1320

tatattctga tggaacagaa gaaagcaata tcaagagaga caaaacacac actttgatga   1380

gctctatctt ttaaacaaaa aatggaattg aaagaccaaa taaaataggc attagcccat   1440
```

-continued

```
atcataaaat cttttgtaaa atattaatag aaagtaaatg aacactatat atgatgcata   1500
cgtagaaaat gtaaaaggat ttttgagata atatcttttg atgttgaatg tgaatgcagg   1560
caacagcagg tttgaggctc ttggatgggg atgctgctga aaagatattg caagcggtaa   1620
ccatgagctt agttcatttc cttatgttat taactacgct ttcaatgtct taactttcgt   1680
tttctctcat gttgaaggtt agggaaatgt tcaggaacag aagttccctg agcgttcaac   1740
ctgatgcagt atctgttatt gatggaaccc aagaaggttc ttacttatgg gtatgactta   1800
cttaaagttt atttttatca gaattcattc taattttttt acttaagaag atggaagaaa   1860
gtgtgatcac attacctagg acattcatct tatttaaaat aatttattgc aaaataatac   1920
tattttttaa ttagaattga tatttgcgta tattgtgaaa aagaaaagta gattgatttt   1980
tcattatggt aaagtatttt aataaatttt tattaactct tttttaactt taaaaaatat   2040
aggatcactt tatgtgtgtg gtgacatgcc ataccccata tggacaatta ctgacatgcc   2100
atacccgata tattaatatt ttatcaattg tcaatttatt tattgtaact actttaaaaa   2160
atacttttaa ttaaatcatt gaggtatcgc tttagttttt ttttaaattc gaaaaaataa   2220
ttaataatta ttagatatac tggaagaatt tccgaaggat attcatatcc atatatatct   2280
tgtaagataa catttttat tgaacaaatg caacactatc tctaaatatg atttttttat   2340
ttatgtcgaa tgaatcacga cgatataatt ttgtataagt aattaaattc actattcatt   2400
tttatttgtt gtgtttcttt tagggtccgc caattagcta aatcttacct aaaaagattg   2460
caaacaaaga aaaaagaaag aagcaatgat gaaattaaaa gtggatcaaa ccatgaggat   2520
atgtttcaaa aagaagaatt aggttctttg ttatgttttc aaaaactagt agttggaatt   2580
tcttaaattc aattataatt atttaataaa attgtctgct taattgataa tataaaatag   2640
cataactgat acatttataa attatatttt atattaaaat ttatttttat tttatagata   2700
aaatgtattt ggtaatattt ataatatagt tttaaattaa tttcaaactt gttgtgatct   2760
tacttataaa ttaattattt ttttcagttt tcaattattg catttttctt ataatattca   2820
ctatattaat atttgacaat atttcaaaac attttcaata aaaaaaaaaa aaaaagaagt   2880
tcagtaaact tcatatctgc attatgttta tttgaatagt aaaacactat aaaatatatc   2940
taatgtaaag gataaacatg cagagtagta aaaaacttat ttagaatata gtcatttaat   3000
ttttcttatg atatatcttg ggaattttgt gtaggttaca gttaactatc tgttaggaaa   3060
gttgggaaag aagtttacaa aaactgtggg agtgatagat cttggaggtg cttcagttca   3120
aatggcttat gctgtctcaa gaaatacagc taaaaatgcc ccaaaaccac cacaaggaga   3180
ggatccatac atgaagaagc ttgtactcaa gggaaagaaa tatgaccttt atgttcacag   3240
gttactttct gttatcattc atatagcaaa ggaacaatta tcatttcaat ttctaaaata   3300
tatttataat ctctaaaatc aaataacata aaaaaatggt aatataatgt tgcgttttgg   3360
gattgtttgg attaaagggt aaatttgaag aagaaaaaaa ataataaata aagaaaaaga   3420
gaaaaaaaat aagattgttt ggattattag aaagagaaaa agttgaataa ttatttttat   3480
attttaatat tattttaatt atttattatt atgaaaataa aatatttatt tttaaattta   3540
tattttatta ttattttta attttattat tataaaaata taaatattat taataattat   3600
tattttaatt ttatttatta atataatata ataataaata aaatattaat attttatgtt   3660
atattatata atatttaatt atacatatgt atttttttc tgcaaatttt taccttttaa   3720
gcggagaaga tgaagggcat aaattgttct cgaaattagt tatattttgt tcaattttaa   3780
caaaatcatc tcaaatcagt cttcataaat agtatttatg tagatccaaa tagaggctta   3840
```

-continued

```
acgtggtcta gttgtacaaa cctaaaaggt gtttcttttt ttctttaatt tgaagaacta   3900
gaatattgtt tttcaatttg aaagacgaag gcaaacttaa ccaaatttag aaaaagtaaa   3960
aacttggtta actttataac gaatgtcaga aaaaatggta ggtatgttat aaatacttct   4020
gatatcaaaa tggcaaaaac tccagagtct cacttccaag aatcatcact ttttctcacc   4080
ttaatctgaa ataatgaatg cttacttttt ttaagatatt tatagatatc tataatccat   4140
tgaagttcag tgtagtgtaa ataaattata atgtaaaaac ctatacactg agtacagatc   4200
catgtgtagt tacttttta tggtttaact gataaatatg catgagtcat gtcatggcta   4260
acgtacaggt cttaatcaac ttctttgttg cagttacttg cgttatggta acgacgcagc   4320
acgtgttaag atttttaaga ccactgatgg tgctgctagt ccttgcctat tggcaggcta   4380
tgaaggtaaa taaagtattc ttttgtacaa accctaatgt tactttctta ttcctgcatt   4440
cagaatagtg caaaggactg aaactagaaa ggattccaat tcactacaag aagaaaaaaa   4500
agtagtgatt tagtgaccaa agttactttt tcctcactga gttctattga aatgcagaaa   4560
cttgttgcag atattttaaa tacatattaa gtgttttgtc agtactgcat ttgtttttag   4620
tgatttcaag tcgagttttt tcttgaagca ttaaagctgc aaataacatg tgggtctttt   4680
ttctatcttt aaagatatat acagatattc cggagaatcg tacaatatct atggtcccac   4740
ttctggtgcc aactttaatg agtgccgtga cctagctctt cagattctca gattgaatga   4800
gccatgttcc catgaaaact gcacctttgg tgggatatgg gatggtggaa aaggaagtgg   4860
acagaaaaac cttgttgtta cttcagcttt ctactatagg tcttctgagg tatccattct   4920
ctgttaattt cttgtttact ttgattactt atttgttttt ataccaataa attttacatt   4980
atagtttata ctgtgctaat tttgttgttt ttaggttggt tttgtcactc ctcccaattc   5040
caaaaatcgc cctctggatt ttgaaactgc agctaaacaa gcttgtagtt taacattcga   5100
ggaagcgaaa tccacttttc caaatgttga gaaagataaa cttccatttg tatgcgtgga   5160
tttcacatac cagtatacat tgcttgttga tggatttggt atgttttcat aattaattac   5220
caagttgata tttaacttct tccaaaaaac tatgttttct tttgtcttcc aacactgact   5280
cctaattcaa cttttggcag gcctagatcc agagcaagag attacagtgg cagaaggaat   5340
tgaatatcaa gatgccattg tggaaacagc atggcctcta ggaactgcca tagaagccat   5400
atcatctttg cctaaattta atcgtctaat gtattttatc taagccatgt cctccactta   5460
tgaccacttt aattaaaata aaactcaccc ttttcactag tcctttttta ttccattgag   5520
tatcaagtgt taatttgttt ctgacaaatg gaggtgtaaa agtgaaacaa agtatgtttt   5580
tgtcagatac gaatggaagt agggttatga tgacctgcca attaactaat actctgactt   5640
ctttcatcct cttattttaa ttttgaaaaa aaaaatcata tatgtaatcg ggaaaatttg   5700
atttgcaact taaaaaaatg accaaataaa ttttcctaaa ttcctctgca acatatacaa   5760
ggaccacaaa attgaatctg tttctttaat ggaataagta ctttttgaaa aactatcata   5820
ttagtaaact tatctttttc atctaacagg cagcaaaatt aattgcatga acggatccaa   5880
ttaattctct cgtacagctc cagataagaa gcgtttaatg agataaattg ttggataata   5940
tatgttgggt gtgggtggat tatgatacta tcgataataa atttggaatc taattaaatt   6000
ttataaaatt aatttatcaa tatataatat tttatatata ttaatttgat aatattttta   6060
ataattttat atttttaata tttaatttta atttaaggaa atttttaaga taattaattt   6120
tttattttta tttttttgta tagtactcag gacataataa tgttattaat ttaaataaga   6180
```

```
cttaaatata tatttttctt ataatgctta aatctcagtc ttattattgc tatcacataa   6240

tgacacgaac taactagctt cactc                                         6265


<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:degenerate
      5' PCR primer
<221> NAME/KEY: modified_base
<222> LOCATION: (6)
<223> OTHER INFORMATION: n = g, a, c or t
<221> NAME/KEY: modified_base
<222> LOCATION: (9)
<223> OTHER INFORMATION: n = g, a, c or t

<400> SEQUENCE: 4

taygcngtna tyttygatcg                                                 20


<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:degenerate
      3' PCR primer
<221> NAME/KEY: modified_base
<222> LOCATION: (15)
<223> OTHER INFORMATION: n = g, a, c or t

<400> SEQUENCE: 5

atrttrtada trccngg                                                    17


<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence:5' RACE
      primer

<400> SEQUENCE: 6

cgtccgatac ttctata                                                    17


<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:3' RACE
      primer

<400> SEQUENCE: 7

aacttagatc tcctgcac                                                   18


<210> SEQ ID NO 8
<211> LENGTH: 1458
<212> TYPE: DNA
<213> ORGANISM: Medicago sativa
<220> FEATURE:
<221> NAME/KEY: CDS
<222> LOCATION: (1)..(1458)
<223> OTHER INFORMATION: full length clone
<221> NAME/KEY: CDS
<222> LOCATION: (13)..(1380)
<223> OTHER INFORMATION: NBP46
<221> NAME/KEY: modified_base
<222> LOCATION: (1)..(1458)
```

```
<223> OTHER INFORMATION: n = g, a, c or t

<400> SEQUENCE: 8

caa att aag aac atg gag ttc cta att aca ctc att gcc act ttt tta       48
Gln Ile Lys Asn Met Glu Phe Leu Ile Thr Leu Ile Ala Thr Phe Leu
  1               5                  10                  15

ctc ttg tta atg cct gca atc act tcc tcc caa tat tta gga aac aac       96
Leu Leu Leu Met Pro Ala Ile Thr Ser Ser Gln Tyr Leu Gly Asn Asn
             20                  25                  30

cta ctc act aat cga aag att ttc caa aaa caa gaa acc tta acc tct      144
Leu Leu Thr Asn Arg Lys Ile Phe Gln Lys Gln Glu Thr Leu Thr Ser
         35                  40                  45

tac gct gtc ata ttt gat gct ggt agc act ggt act cgt gtc cat gtt      192
Tyr Ala Val Ile Phe Asp Ala Gly Ser Thr Gly Thr Arg Val His Val
     50                  55                  60

tac cat ttt gat cag aac tta gat cta ctt cac att ggc aat gat att      240
Tyr His Phe Asp Gln Asn Leu Asp Leu Leu His Ile Gly Asn Asp Ile
 65                  70                  75                  80

gag ttt gtt gac aag atc aaa cca ggt ttg agt gca tat ggg gat aat      288
Glu Phe Val Asp Lys Ile Lys Pro Gly Leu Ser Ala Tyr Gly Asp Asn
                 85                  90                  95

cct gaa caa gca gca aaa tct ctc att cca ctt ttg gag gaa gca gaa      336
Pro Glu Gln Ala Ala Lys Ser Leu Ile Pro Leu Leu Glu Glu Ala Glu
            100                 105                 110

gat gtg gtt cct gag gat ctg cac ccc aaa aca ccc ctt agg ctt ggg      384
Asp Val Val Pro Glu Asp Leu His Pro Lys Thr Pro Leu Arg Leu Gly
        115                 120                 125

gca acc gca ggt ttg agg ctt ttg aat ggg gat gct gct gaa aag ata      432
Ala Thr Ala Gly Leu Arg Leu Leu Asn Gly Asp Ala Ala Glu Lys Ile
    130                 135                 140

ttg caa gcg aca agg aat atg ttc agc aac aga agt acc ctc aac gtt      480
Leu Gln Ala Thr Arg Asn Met Phe Ser Asn Arg Ser Thr Leu Asn Val
145                 150                 155                 160

caa cgt gat gca gtt tct att att gat gga acc caa gaa ggt tct tat      528
Gln Arg Asp Ala Val Ser Ile Ile Asp Gly Thr Gln Glu Gly Ser Tyr
                165                 170                 175

atg tgg gtg aca gtt aac tat gta ttg ggg aat ttg gga aaa agc ttc      576
Met Trp Val Thr Val Asn Tyr Val Leu Gly Asn Leu Gly Lys Ser Phe
            180                 185                 190

aca aaa tca gtg gga gta att gac ctt gga ggt ggt tca gtt caa atg      624
Thr Lys Ser Val Gly Val Ile Asp Leu Gly Gly Gly Ser Val Gln Met
        195                 200                 205

aca tat gca gtg tca aag aaa aca gca aaa aat gct cct aaa gtt gct      672
Thr Tyr Ala Val Ser Lys Lys Thr Ala Lys Asn Ala Pro Lys Val Ala
    210                 215                 220

gat gga gag gat cca tat att aag aag ctt gtg ctc aag gga aag caa      720
Asp Gly Glu Asp Pro Tyr Ile Lys Lys Leu Val Leu Lys Gly Lys Gln
225                 230                 235                 240

tat gat ctc tat gtt cat agt tac ttg cgt ttt ggc aaa gaa gca act      768
Tyr Asp Leu Tyr Val His Ser Tyr Leu Arg Phe Gly Lys Glu Ala Thr
                245                 250                 255

cga gca cag gtt ttg aat gca act aat gga tct gct aac cct tgc att      816
Arg Ala Gln Val Leu Asn Ala Thr Asn Gly Ser Ala Asn Pro Cys Ile
            260                 265                 270

tta cct gga ttt aat ggg acc ttt aca tat tca gga gtg gag tat aag      864
Leu Pro Gly Phe Asn Gly Thr Phe Thr Tyr Ser Gly Val Glu Tyr Lys
        275                 280                 285

gct ttt tcc cct tct tct ggc tcc aac ttt gat gat tgc aaa gaa ata      912
Ala Phe Ser Pro Ser Ser Gly Ser Asn Phe Asp Asp Cys Lys Glu Ile
    290                 295                 300
```

-continued

```
att ctt aag gtt ctt aaa gta aat gat cca tgt ccc tat ccg agt tgc      960
Ile Leu Lys Val Leu Lys Val Asn Asp Pro Cys Pro Tyr Pro Ser Cys
305                 310                 315                 320

act ttt ggt gga ata tgg aat ggt gga gga ggg agt gga caa aaa aaa     1008
Thr Phe Gly Gly Ile Trp Asn Gly Gly Gly Gly Ser Gly Gln Lys Lys
                325                 330                 335

ctt ttt gtt act tca gct ttc gct tac ctg gct gaa gat gtt ggt atg     1056
Leu Phe Val Thr Ser Ala Phe Ala Tyr Leu Ala Glu Asp Val Gly Met
            340                 345                 350

gtt gag cca aat aaa cct aat tcc ata ctt cat cca gta gat ttc gaa     1104
Val Glu Pro Asn Lys Pro Asn Ser Ile Leu His Pro Val Asp Phe Glu
        355                 360                 365

att gaa gct aag cga gct tgt gca tta aac ttt gag gat gtc aaa tcc     1152
Ile Glu Ala Lys Arg Ala Cys Ala Leu Asn Phe Glu Asp Val Lys Ser
    370                 375                 380

act tat cct cga ctt acg gat gca aaa cgt cca tat gta tgc atg gat     1200
Thr Tyr Pro Arg Leu Thr Asp Ala Lys Arg Pro Tyr Val Cys Met Asp
385                 390                 395                 400

ctc tta tac caa cat gtg ttg ctt gtt cat gga ttt ggc tta ggt cca     1248
Leu Leu Tyr Gln His Val Leu Leu Val His Gly Phe Gly Leu Gly Pro
                405                 410                 415

cga aaa gag att aca gta ggt gag gga att caa tat cag aat tct gtt     1296
Arg Lys Glu Ile Thr Val Gly Glu Gly Ile Gln Tyr Gln Asn Ser Val
            420                 425                 430

gtg gaa gct gca tgg cct cta ggt act gcc gtg gaa gcc ata tca gcg     1344
Val Glu Ala Ala Trp Pro Leu Gly Thr Ala Val Glu Ala Ile Ser Ala
        435                 440                 445

tta cct aag ttt aag cga tta atg tat ttt att taa gct ttt aga gat     1392
Leu Pro Lys Phe Lys Arg Leu Met Tyr Phe Ile     Ala Phe Arg Asp
    450                 455                 460

gtc aag ata ttt cag taa cag cta act tta tca aaa att aaa taa aac     1440
Val Lys Ile Phe Gln     Gln Leu Thr Leu Ser Lys Ile Lys     Asn
465                 470                 475                 480

tgg cgc att ttg tct ttc                                             1458
Trp Arg Ile Leu Ser Phe
                485


<210> SEQ ID NO 9
<211> LENGTH: 459
<212> TYPE: PRT
<213> ORGANISM: Medicago sativa
<220> FEATURE:
<221> NAME/KEY: MOD_RES
<222> LOCATION: (1)..(459)
<223> OTHER INFORMATION: Xaa = any amino acid

<400> SEQUENCE: 9

Gln Ile Lys Asn Met Glu Phe Leu Ile Thr Leu Ile Ala Thr Phe Leu
  1               5                  10                  15

Leu Leu Leu Met Pro Ala Ile Thr Ser Ser Gln Tyr Leu Gly Asn Asn
             20                  25                  30

Leu Leu Thr Asn Arg Lys Ile Phe Gln Lys Gln Glu Thr Leu Thr Ser
         35                  40                  45

Tyr Ala Val Ile Phe Asp Ala Gly Ser Thr Gly Thr Arg Val His Val
     50                  55                  60

Tyr His Phe Asp Gln Asn Leu Asp Leu Leu His Ile Gly Asn Asp Ile
 65                  70                  75                  80

Glu Phe Val Asp Lys Ile Lys Pro Gly Leu Ser Ala Tyr Gly Asp Asn
                 85                  90                  95
```

-continued

```
Pro Glu Gln Ala Ala Lys Ser Leu Ile Pro Leu Leu Glu Glu Ala Glu
            100                 105                 110

Asp Val Val Pro Glu Asp Leu His Pro Lys Thr Pro Leu Arg Leu Gly
        115                 120                 125

Ala Thr Ala Gly Leu Arg Leu Leu Asn Gly Asp Ala Ala Glu Lys Ile
    130                 135                 140

Leu Gln Ala Thr Arg Asn Met Phe Ser Asn Arg Ser Thr Leu Asn Val
145                 150                 155                 160

Gln Arg Asp Ala Val Ser Ile Ile Asp Gly Thr Gln Glu Gly Ser Tyr
                165                 170                 175

Met Trp Val Thr Val Asn Tyr Val Leu Gly Asn Leu Gly Lys Ser Phe
            180                 185                 190

Thr Lys Ser Val Gly Val Ile Asp Leu Gly Gly Gly Ser Val Gln Met
        195                 200                 205

Thr Tyr Ala Val Ser Lys Lys Thr Ala Lys Asn Ala Pro Lys Val Ala
    210                 215                 220

Asp Gly Glu Asp Pro Tyr Ile Lys Lys Leu Val Leu Lys Gly Lys Gln
225                 230                 235                 240

Tyr Asp Leu Tyr Val His Ser Tyr Leu Arg Phe Gly Lys Glu Ala Thr
                245                 250                 255

Arg Ala Gln Val Leu Asn Ala Thr Asn Gly Ser Ala Asn Pro Cys Ile
            260                 265                 270

Leu Pro Gly Phe Asn Gly Thr Phe Thr Tyr Ser Gly Val Glu Tyr Lys
        275                 280                 285

Ala Phe Ser Pro Ser Ser Gly Ser Asn Phe Asp Asp Cys Lys Glu Ile
    290                 295                 300

Ile Leu Lys Val Leu Lys Val Asn Asp Pro Cys Pro Tyr Pro Ser Cys
305                 310                 315                 320

Thr Phe Gly Gly Ile Trp Asn Gly Gly Gly Gly Ser Gly Gln Lys Lys
                325                 330                 335

Leu Phe Val Thr Ser Ala Phe Ala Tyr Leu Ala Glu Asp Val Gly Met
            340                 345                 350

Val Glu Pro Asn Lys Pro Asn Ser Ile Leu His Pro Val Asp Phe Glu
        355                 360                 365

Ile Glu Ala Lys Arg Ala Cys Ala Leu Asn Phe Glu Asp Val Lys Ser
    370                 375                 380

Thr Tyr Pro Arg Leu Thr Asp Ala Lys Arg Pro Tyr Val Cys Met Asp
385                 390                 395                 400

Leu Leu Tyr Gln His Val Leu Leu Val His Gly Phe Gly Leu Gly Pro
                405                 410                 415

Arg Lys Glu Ile Thr Val Gly Glu Gly Ile Gln Tyr Gln Asn Ser Val
            420                 425                 430

Val Glu Ala Ala Trp Pro Leu Gly Thr Ala Val Glu Ala Ile Ser Ala
        435                 440                 445

Leu Pro Lys Phe Lys Arg Leu Met Tyr Phe Ile
    450                 455
```

<210> SEQ ID NO 10
<211> LENGTH: 9
<212> TYPE: PRT
<213> ORGANISM: Medicago sativa

<400> SEQUENCE: 10

```
Ala Phe Arg Asp Val Lys Ile Phe Gln
  1               5
```

<210> SEQ ID NO 11
<211> LENGTH: 8
<212> TYPE: PRT
<213> ORGANISM: Medicago sativa

<400> SEQUENCE: 11

```
Gln Leu Thr Leu Ser Lys Ile Lys
  1               5
```

<210> SEQ ID NO 12
<211> LENGTH: 7
<212> TYPE: PRT
<213> ORGANISM: Medicago sativa

<400> SEQUENCE: 12

```
Asn Trp Arg Ile Leu Ser Phe
  1               5
```

<210> SEQ ID NO 13
<211> LENGTH: 1489
<212> TYPE: DNA
<213> ORGANISM: Lotus japonicus
<220> FEATURE:
<221> NAME/KEY: CDS
<222> LOCATION: (1)..(1488)
<223> OTHER INFORMATION: full length clone
<221> NAME/KEY: CDS
<222> LOCATION: (43)..(1413)
<223> OTHER INFORMATION: NBP46

<400> SEQUENCE: 13

```
aag tgc tct tct ctc tgt agt tag ttg cat tgg act aaa gcc atg gac       48
Lys Cys Ser Ser Leu Cys Ser     Leu His Trp Thr Lys Ala Met Asp
  1               5                  10                  15

ttc tta att agt ctc atg acc ttt gtg ttc atg tta atg cct gct atc       96
Phe Leu Ile Ser Leu Met Thr Phe Val Phe Met Leu Met Pro Ala Ile
             20                  25                  30

tct tcc tcc caa tat ctc gga aac aac att ctc atg aat cgt aag ata      144
Ser Ser Ser Gln Tyr Leu Gly Asn Asn Ile Leu Met Asn Arg Lys Ile
         35                  40                  45

tta ctc ccc aaa aat cag gaa cca gtt aca tca tac gct gtt ata ttt      192
Leu Leu Pro Lys Asn Gln Glu Pro Val Thr Ser Tyr Ala Val Ile Phe
     50                  55                  60

gat gct ggt agc act gga agc aga gtc cat gtc tac aat ttt gat cag      240
Asp Ala Gly Ser Thr Gly Ser Arg Val His Val Tyr Asn Phe Asp Gln
 65                  70                  75                  80

aac tta gat ctc ctt ccc gtt gaa aac gaa ctt gag ttt tat gat tcg      288
Asn Leu Asp Leu Leu Pro Val Glu Asn Glu Leu Glu Phe Tyr Asp Ser
                 85                  90                  95

gtt aaa ccc ggt ttg agt tca tac gct gct aat cct gaa gaa gct gca      336
Val Lys Pro Gly Leu Ser Ser Tyr Ala Ala Asn Pro Glu Glu Ala Ala
            100                 105                 110

gaa tct ctg att cca ctt cta aaa gaa gca gaa aat gtg gtt cct gtg      384
Glu Ser Leu Ile Pro Leu Leu Lys Glu Ala Glu Asn Val Val Pro Val
        115                 120                 125

agc cag caa ccc aac aca ccc gtt aag ctt ggg gca act gca ggt tta      432
Ser Gln Gln Pro Asn Thr Pro Val Lys Leu Gly Ala Thr Ala Gly Leu
    130                 135                 140

agg ctt ttg gag ggg aat gct gct gaa aat ata ttg caa gcg gtc agg      480
Arg Leu Leu Glu Gly Asn Ala Ala Glu Asn Ile Leu Gln Ala Val Arg
145                 150                 155                 160

gat atg ctc agc aac aga agt gcc ctt aat gtt caa tca gat gca gta      528
```

-continued

```
Asp Met Leu Ser Asn Arg Ser Ala Leu Asn Val Gln Ser Asp Ala Val
            165                 170                 175

tct att ctt gat gga acc caa gaa ggt tct tat ctt tgg gtg aca att      576
Ser Ile Leu Asp Gly Thr Gln Glu Gly Ser Tyr Leu Trp Val Thr Ile
        180                 185                 190

aac tat ctc ttg ggg aag ttg gga aaa aga ttt aca aag aca gtg gga      624
Asn Tyr Leu Leu Gly Lys Leu Gly Lys Arg Phe Thr Lys Thr Val Gly
    195                 200                 205

gta gtt gat cta gga ggt ggg tca gtg caa atg aca tat gca gtc tca      672
Val Val Asp Leu Gly Gly Gly Ser Val Gln Met Thr Tyr Ala Val Ser
    210                 215                 220

agg aac aca gct aaa aat gct cca aaa gta cct gaa gga gag gat cca      720
Arg Asn Thr Ala Lys Asn Ala Pro Lys Val Pro Glu Gly Glu Asp Pro
225                 230                 235                 240

tac ata aag aag ctt gta ctc cag gga aag aaa tat gac ctt tat gtt      768
Tyr Ile Lys Lys Leu Val Leu Gln Gly Lys Lys Tyr Asp Leu Tyr Val
                245                 250                 255

cac agt tac ttg cgc tat gga aga gaa gca ttt cgt gca gag att ttc      816
His Ser Tyr Leu Arg Tyr Gly Arg Glu Ala Phe Arg Ala Glu Ile Phe
            260                 265                 270

aag gtc gct ggt ggt tct gct aat cct tgc att tta gct ggc ttt gat      864
Lys Val Ala Gly Gly Ser Ala Asn Pro Cys Ile Leu Ala Gly Phe Asp
        275                 280                 285

ggg gca tat aca tat tcc gga gca gag tat aag gtc tcg gcc cca gct      912
Gly Ala Tyr Thr Tyr Ser Gly Ala Glu Tyr Lys Val Ser Ala Pro Ala
    290                 295                 300

tca gga tct aac ttg aat caa tgc aga aag ata gct ctt aag gct ctt      960
Ser Gly Ser Asn Leu Asn Gln Cys Arg Lys Ile Ala Leu Lys Ala Leu
305                 310                 315                 320

aaa gtg aat gca cct tgt ccc tat cag aat tgc act ttt ggt ggg ata     1008
Lys Val Asn Ala Pro Cys Pro Tyr Gln Asn Cys Thr Phe Gly Gly Ile
                325                 330                 335

tgg aat ggt gga ggt gga agt ggt caa aaa aat ctt ttc ctt act tca     1056
Trp Asn Gly Gly Gly Gly Ser Gly Gln Lys Asn Leu Phe Leu Thr Ser
            340                 345                 350

tct ttc tat tac ctc tct gaa gat gtt ggg atc ttt gtg aat aaa ccc     1104
Ser Phe Tyr Tyr Leu Ser Glu Asp Val Gly Ile Phe Val Asn Lys Pro
        355                 360                 365

aat gcc aaa att cgt cca gtt gat ttg aag act gca gct aaa cta gct     1152
Asn Ala Lys Ile Arg Pro Val Asp Leu Lys Thr Ala Ala Lys Leu Ala
    370                 375                 380

tgt aaa aca aat ctt gag gat gca aaa tcc aaa tac cca gat ctt tat     1200
Cys Lys Thr Asn Leu Glu Asp Ala Lys Ser Lys Tyr Pro Asp Leu Tyr
385                 390                 395                 400

gag aaa gac agt gtt gaa tat gtg tgc ttg gat ctt gtc tac gtg tac     1248
Glu Lys Asp Ser Val Glu Tyr Val Cys Leu Asp Leu Val Tyr Val Tyr
                405                 410                 415

aca ttg ctt gtt gat gga ttt ggt ctt gat cca ttt caa gag gtt aca     1296
Thr Leu Leu Val Asp Gly Phe Gly Leu Asp Pro Phe Gln Glu Val Thr
            420                 425                 430

gtg gcg aat gaa att gaa tat cag gat gct ctt gtg gaa gcc gca tgg     1344
Val Ala Asn Glu Ile Glu Tyr Gln Asp Ala Leu Val Glu Ala Ala Trp
        435                 440                 445

cct cta ggc act gcc ata gaa gca ata tca tca ttg cct aaa ttt gag     1392
Pro Leu Gly Thr Ala Ile Glu Ala Ile Ser Ser Leu Pro Lys Phe Glu
    450                 455                 460

aga tta atg tat ttt att taa act act agt acc tgc tta agc ctg gat     1440
Arg Leu Met Tyr Phe Ile     Thr Thr Ser Thr Cys Leu Ser Leu Asp
465                 470                 475                 480
```

-continued

```
tac ctg aag aaa taa aat gaa ata aaa gcc gca tct ttc ttc ctt gct t   1489
Tyr Leu Lys Lys     Asn Glu Ile Lys Ala Ala Ser Phe Phe Leu Ala
                485                 490                 495
```

<210> SEQ ID NO 14
<211> LENGTH: 7
<212> TYPE: PRT
<213> ORGANISM: Lotus japonicus

<400> SEQUENCE: 14

```
Lys Cys Ser Ser Leu Cys Ser
  1               5
```

<210> SEQ ID NO 15
<211> LENGTH: 462
<212> TYPE: PRT
<213> ORGANISM: Lotus japonicus

<400> SEQUENCE: 15

```
Leu His Trp Thr Lys Ala Met Asp Phe Leu Ile Ser Leu Met Thr Phe
  1               5                  10                  15

Val Phe Met Leu Met Pro Ala Ile Ser Ser Ser Gln Tyr Leu Gly Asn
             20                  25                  30

Asn Ile Leu Met Asn Arg Lys Ile Leu Leu Pro Lys Asn Gln Glu Pro
         35                  40                  45

Val Thr Ser Tyr Ala Val Ile Phe Asp Ala Gly Ser Thr Gly Ser Arg
     50                  55                  60

Val His Val Tyr Asn Phe Asp Gln Asn Leu Asp Leu Leu Pro Val Glu
 65                  70                  75                  80

Asn Glu Leu Glu Phe Tyr Asp Ser Val Lys Pro Gly Leu Ser Ser Tyr
                 85                  90                  95

Ala Ala Asn Pro Glu Glu Ala Ala Glu Ser Leu Ile Pro Leu Leu Lys
            100                 105                 110

Glu Ala Glu Asn Val Val Pro Val Ser Gln Gln Pro Asn Thr Pro Val
        115                 120                 125

Lys Leu Gly Ala Thr Ala Gly Leu Arg Leu Leu Glu Gly Asn Ala Ala
    130                 135                 140

Glu Asn Ile Leu Gln Ala Val Arg Asp Met Leu Ser Asn Arg Ser Ala
145                 150                 155                 160

Leu Asn Val Gln Ser Asp Ala Val Ser Ile Leu Asp Gly Thr Gln Glu
                165                 170                 175

Gly Ser Tyr Leu Trp Val Thr Ile Asn Tyr Leu Leu Gly Lys Leu Gly
            180                 185                 190

Lys Arg Phe Thr Lys Thr Val Gly Val Val Asp Leu Gly Gly Gly Ser
        195                 200                 205

Val Gln Met Thr Tyr Ala Val Ser Arg Asn Thr Ala Lys Asn Ala Pro
    210                 215                 220

Lys Val Pro Glu Gly Glu Asp Pro Tyr Ile Lys Lys Leu Val Leu Gln
225                 230                 235                 240

Gly Lys Lys Tyr Asp Leu Tyr Val His Ser Tyr Leu Arg Tyr Gly Arg
                245                 250                 255

Glu Ala Phe Arg Ala Glu Ile Phe Lys Val Ala Gly Gly Ser Ala Asn
            260                 265                 270

Pro Cys Ile Leu Ala Gly Phe Asp Gly Ala Tyr Thr Tyr Ser Gly Ala
        275                 280                 285

Glu Tyr Lys Val Ser Ala Pro Ala Ser Gly Ser Asn Leu Asn Gln Cys
    290                 295                 300
```

```
Arg Lys Ile Ala Leu Lys Ala Leu Lys Val Asn Ala Pro Cys Pro Tyr
305                 310                 315                 320

Gln Asn Cys Thr Phe Gly Gly Ile Trp Asn Gly Gly Gly Gly Ser Gly
                325                 330                 335

Gln Lys Asn Leu Phe Leu Thr Ser Ser Phe Tyr Tyr Leu Ser Glu Asp
            340                 345                 350

Val Gly Ile Phe Val Asn Lys Pro Asn Ala Lys Ile Arg Pro Val Asp
        355                 360                 365

Leu Lys Thr Ala Ala Lys Leu Ala Cys Lys Thr Asn Leu Glu Asp Ala
    370                 375                 380

Lys Ser Lys Tyr Pro Asp Leu Tyr Glu Lys Asp Ser Val Glu Tyr Val
385                 390                 395                 400

Cys Leu Asp Leu Val Tyr Val Tyr Thr Leu Leu Val Asp Gly Phe Gly
                405                 410                 415

Leu Asp Pro Phe Gln Glu Val Thr Val Ala Asn Glu Ile Glu Tyr Gln
            420                 425                 430

Asp Ala Leu Val Glu Ala Ala Trp Pro Leu Gly Thr Ala Ile Glu Ala
        435                 440                 445

Ile Ser Ser Leu Pro Lys Phe Glu Arg Leu Met Tyr Phe Ile
    450                 455                 460


<210> SEQ ID NO 16
<211> LENGTH: 13
<212> TYPE: PRT
<213> ORGANISM: Lotus japonicus

<400> SEQUENCE: 16

Thr Thr Ser Thr Cys Leu Ser Leu Asp Tyr Leu Lys Lys
  1               5                  10


<210> SEQ ID NO 17
<211> LENGTH: 11
<212> TYPE: PRT
<213> ORGANISM: Lotus japonicus

<400> SEQUENCE: 17

Asn Glu Ile Lys Ala Ala Ser Phe Phe Leu Ala
  1               5                  10


<210> SEQ ID NO 18
<211> LENGTH: 1434
<212> TYPE: DNA
<213> ORGANISM: Dolichos biflorus
<220> FEATURE:
<221> NAME/KEY: CDS
<222> LOCATION: (1)..(1404)
<223> OTHER INFORMATION: DBX gene involved in oligosaccharide signaling
<221> NAME/KEY: sig_peptide
<222> LOCATION: (1)..(60)
<221> NAME/KEY: mat_peptide
<222> LOCATION: (61)..(1404)
<221> NAME/KEY: primer_bind
<222> LOCATION: Complement((1)..(22))
<223> OTHER INFORMATION: DBXtop primer
<221> NAME/KEY: primer_bind
<222> LOCATION: (274)..(291)
<223> OTHER INFORMATION: DBX8 primer
<221> NAME/KEY: primer_bind
<222> LOCATION: (297)..(314)
<223> OTHER INFORMATION: DBX7-for/rev primer
<221> NAME/KEY: primer_bind
<222> LOCATION: (667)..(685)
<223> OTHER INFORMATION: DBX1-for/rev primer
<221> NAME/KEY: primer_bind
```

```
<222> LOCATION: (688)..(704)
<223> OTHER INFORMATION: DBX2-for/rev primer
<221> NAME/KEY: primer_bind
<222> LOCATION: Complement((766)..(785))
<223> OTHER INFORMATION: DBX10 primer
<221> NAME/KEY: misc_feature
<222> LOCATION: (856)..(857)
<223> OTHER INFORMATION: splice site
<221> NAME/KEY: primer_bind
<222> LOCATION: (857)..(872)
<223> OTHER INFORMATION: DBX6 primer
<221> NAME/KEY: primer_bind
<222> LOCATION: (878)..(896)
<223> OTHER INFORMATION: DBX5 primer
<221> NAME/KEY: primer_bind
<222> LOCATION: (933)..(952)
<223> OTHER INFORMATION: DBX3 primer
<221> NAME/KEY: primer_bind
<222> LOCATION: (955)..(972)
<223> OTHER INFORMATION: DBX4 primer
<221> NAME/KEY: misc_feature
<222> LOCATION: (1071)..(1072)
<223> OTHER INFORMATION: splice site
<221> NAME/KEY: primer_bind
<222> LOCATION: Complement((1075)..(1093))
<223> OTHER INFORMATION: DBX11 primer
<221> NAME/KEY: primer_bind
<222> LOCATION: (1133)..(1151)
<223> OTHER INFORMATION: DBX9-for/rev primer
<221> NAME/KEY: primer_bind
<222> LOCATION: (1227)..(1247)
<223> OTHER INFORMATION: DBX12 primer
<221> NAME/KEY: primer_bind
<222> LOCATION: (1414)..(1434)
<223> OTHER INFORMATION: DBXbottom primer

<400> SEQUENCE: 18

atg agc atg gat ttt ctc ata atc cta ttt tct ctt ctt ctc tgg acg       48
Met Ser Met Asp Phe Leu Ile Ile Leu Phe Ser Leu Leu Leu Trp Thr
-20                 -15                 -10                 -5

ctg gtt gca act gca act gca act gca agt tcc ttt tcc ctc cat ggg       96
Leu Val Ala Thr Ala Thr Ala Thr Ala Ser Ser Phe Ser Leu His Gly
            -1   1               5                  10

aag ggc ttc aag cat cgc aag ttt tcc tcc tcc gat aat aat tat tcg      144
Lys Gly Phe Lys His Arg Lys Phe Ser Ser Ser Asp Asn Asn Tyr Ser
        15                  20                  25

att gaa gaa acc att aat gaa tct tat gca gtt atc ttc gat gct ggt      192
Ile Glu Glu Thr Ile Asn Glu Ser Tyr Ala Val Ile Phe Asp Ala Gly
    30                  35                  40

agc aca gga agc cgt gta cac gtt tac cgt ttc aac cag caa cta gat      240
Ser Thr Gly Ser Arg Val His Val Tyr Arg Phe Asn Gln Gln Leu Asp
 45                  50                  55                  60

ctt ctt cgc att ggc cat gac ctt gag ctg ttc gtc aag acg aag cca      288
Leu Leu Arg Ile Gly His Asp Leu Glu Leu Phe Val Lys Thr Lys Pro
                65                  70                  75

ggt tta agt gca tac gct gag aat cca gaa gaa gcc gca gaa tct ctt      336
Gly Leu Ser Ala Tyr Ala Glu Asn Pro Glu Glu Ala Ala Glu Ser Leu
            80                  85                  90

gtg cca ctt ttg gag gaa gca gaa gct gtt att cct caa gag ttg cat      384
Val Pro Leu Leu Glu Glu Ala Glu Ala Val Ile Pro Gln Glu Leu His
        95                 100                 105

ccc aga aca ccc gtt aaa gtt gga gca acc gca ggt tta agg caa ttg      432
Pro Arg Thr Pro Val Lys Val Gly Ala Thr Ala Gly Leu Arg Gln Leu
    110                 115                 120

gaa ggg gat gct tcc aac aga atc ttg caa gcg gta agt gat atg ctg      480
Glu Gly Asp Ala Ser Asn Arg Ile Leu Gln Ala Val Ser Asp Met Leu
125                 130                 135                 140

aag aag aga agc aca ttg aag gtt gag ggc gat gca gtt tca gtg ttg      528
```

-continued

```
Lys Lys Arg Ser Thr Leu Lys Val Glu Gly Asp Ala Val Ser Val Leu
                145                 150                 155

agt gga aac caa gaa gga gct tat caa tgg gtg act att aac tat tta      576
Ser Gly Asn Gln Glu Gly Ala Tyr Gln Trp Val Thr Ile Asn Tyr Leu
            160                 165                 170

ctg gga aac ttg gga aag cat tat tca aag acg gtt gct gta gtt gac      624
Leu Gly Asn Leu Gly Lys His Tyr Ser Lys Thr Val Ala Val Val Asp
        175                 180                 185

cta ggt ggt gga tct gtt caa atg gct tac gca atc tca gag gaa gat      672
Leu Gly Gly Gly Ser Val Gln Met Ala Tyr Ala Ile Ser Glu Glu Asp
    190                 195                 200

gct gct aaa gct cca caa gtc cca gac gga gtg gaa tca tac ata acc      720
Ala Ala Lys Ala Pro Gln Val Pro Asp Gly Val Glu Ser Tyr Ile Thr
205                 210                 215                 220

gag atg ttc ctc agg gga aag aaa tat tac ctc tat gta cac agt tac      768
Glu Met Phe Leu Arg Gly Lys Lys Tyr Tyr Leu Tyr Val His Ser Tyr
                225                 230                 235

ttg cgt tat ggt ttg cta gca gct cgt gca gag gtt tta aag gtt tct      816
Leu Arg Tyr Gly Leu Leu Ala Ala Arg Ala Glu Val Leu Lys Val Ser
            240                 245                 250

cgt gat tca gaa aac cct tgt att ttg tct ggt ttt gat ggg tat tac      864
Arg Asp Ser Glu Asn Pro Cys Ile Leu Ser Gly Phe Asp Gly Tyr Tyr
        255                 260                 265

aca tac gga gga gtg cag tat aaa gcc aca gct ccc cct tca ggc tca      912
Thr Tyr Gly Gly Val Gln Tyr Lys Ala Thr Ala Pro Pro Ser Gly Ser
    270                 275                 280

agc ttc agc aaa tgc caa aat gtt gtt ctt gaa gct ctc cat gtc aat      960
Ser Phe Ser Lys Cys Gln Asn Val Val Leu Glu Ala Leu His Val Asn
285                 290                 295                 300

gca aca tgc tct tat aag gat tgc act ttc gga ggc ata tgg aat ggc     1008
Ala Thr Cys Ser Tyr Lys Asp Cys Thr Phe Gly Gly Ile Trp Asn Gly
                305                 310                 315

ggt ggt gga gct ggg gaa aac aac ttt ttt gtt gca tca ttt ttc ttt     1056
Gly Gly Gly Ala Gly Glu Asn Asn Phe Phe Val Ala Ser Phe Phe Phe
            320                 325                 330

gaa gtg gcc gat gag gct ggt ttt gtt gat cca aac gat gcc aat gcc     1104
Glu Val Ala Asp Glu Ala Gly Phe Val Asp Pro Asn Asp Ala Asn Ala
        335                 340                 345

ata gtt cgt cct gtg gat ttt gaa gat gca gca aag gtt gct tgt agc     1152
Ile Val Arg Pro Val Asp Phe Glu Asp Ala Ala Lys Val Ala Cys Ser
    350                 355                 360

aca gaa tta aag gat ctc aag tcc gtt ttc cct cgt gtt aag gat gga     1200
Thr Glu Leu Lys Asp Leu Lys Ser Val Phe Pro Arg Val Lys Asp Gly
365                 370                 375                 380

gat gtt cct tac ata tgt ttg gat cta gta tac caa tat aca ttg ctc     1248
Asp Val Pro Tyr Ile Cys Leu Asp Leu Val Tyr Gln Tyr Thr Leu Leu
                385                 390                 395

gtt gat gga ttt ggc att gat ccc cag caa gag att aca ttg gtg agg     1296
Val Asp Gly Phe Gly Ile Asp Pro Gln Gln Glu Ile Thr Leu Val Arg
            400                 405                 410

caa att cag tat cag gat tct ctc gtg gaa gct gca tgg cca cta gga     1344
Gln Ile Gln Tyr Gln Asp Ser Leu Val Glu Ala Ala Trp Pro Leu Gly
        415                 420                 425

agt gcc ata gaa gcc ata tct tcg tta cct aaa ttt gag aaa tta atg     1392
Ser Ala Ile Glu Ala Ile Ser Ser Leu Pro Lys Phe Glu Lys Leu Met
    430                 435                 440

tat ttc ctt taa gctttaaccg aggatccatg tatgtgttgc                    1434
Tyr Phe Leu
445
```

```
<210> SEQ ID NO 19
<211> LENGTH: 467
<212> TYPE: PRT
<213> ORGANISM: Dolichos biflorus

<400> SEQUENCE: 19

Met Ser Met Asp Phe Leu Ile Ile Leu Phe Ser Leu Leu Leu Trp Thr
  1               5                  10                  15

Leu Val Ala Thr Ala Thr Ala Thr Ala Ser Ser Phe Ser Leu His Gly
             20                  25                  30

Lys Gly Phe Lys His Arg Lys Phe Ser Ser Ser Asp Asn Asn Tyr Ser
         35                  40                  45

Ile Glu Glu Thr Ile Asn Glu Ser Tyr Ala Val Ile Phe Asp Ala Gly
     50                  55                  60

Ser Thr Gly Ser Arg Val His Val Tyr Arg Phe Asn Gln Gln Leu Asp
 65                  70                  75                  80

Leu Leu Arg Ile Gly His Asp Leu Glu Leu Phe Val Lys Thr Lys Pro
                 85                  90                  95

Gly Leu Ser Ala Tyr Ala Glu Asn Pro Glu Glu Ala Ala Glu Ser Leu
            100                 105                 110

Val Pro Leu Leu Glu Glu Ala Glu Ala Val Ile Pro Gln Glu Leu His
        115                 120                 125

Pro Arg Thr Pro Val Lys Val Gly Ala Thr Ala Gly Leu Arg Gln Leu
    130                 135                 140

Glu Gly Asp Ala Ser Asn Arg Ile Leu Gln Ala Val Ser Asp Met Leu
145                 150                 155                 160

Lys Lys Arg Ser Thr Leu Lys Val Glu Gly Asp Ala Val Ser Val Leu
                165                 170                 175

Ser Gly Asn Gln Glu Gly Ala Tyr Gln Trp Val Thr Ile Asn Tyr Leu
            180                 185                 190

Leu Gly Asn Leu Gly Lys His Tyr Ser Lys Thr Val Ala Val Val Asp
        195                 200                 205

Leu Gly Gly Gly Ser Val Gln Met Ala Tyr Ala Ile Ser Glu Glu Asp
    210                 215                 220

Ala Ala Lys Ala Pro Gln Val Pro Asp Gly Val Glu Ser Tyr Ile Thr
225                 230                 235                 240

Glu Met Phe Leu Arg Gly Lys Lys Tyr Tyr Leu Tyr Val His Ser Tyr
                245                 250                 255

Leu Arg Tyr Gly Leu Leu Ala Ala Arg Ala Glu Val Leu Lys Val Ser
            260                 265                 270

Arg Asp Ser Glu Asn Pro Cys Ile Leu Ser Gly Phe Asp Gly Tyr Tyr
        275                 280                 285

Thr Tyr Gly Gly Val Gln Tyr Lys Ala Thr Ala Pro Pro Ser Gly Ser
    290                 295                 300

Ser Phe Ser Lys Cys Gln Asn Val Val Leu Glu Ala Leu His Val Asn
305                 310                 315                 320

Ala Thr Cys Ser Tyr Lys Asp Cys Thr Phe Gly Gly Ile Trp Asn Gly
                325                 330                 335

Gly Gly Gly Ala Gly Glu Asn Asn Phe Phe Val Ala Ser Phe Phe Phe
            340                 345                 350

Glu Val Ala Asp Glu Ala Gly Phe Val Asp Pro Asn Asp Ala Asn Ala
        355                 360                 365

Ile Val Arg Pro Val Asp Phe Glu Asp Ala Ala Lys Val Ala Cys Ser
    370                 375                 380
```

-continued

```
Thr Glu Leu Lys Asp Leu Lys Ser Val Phe Pro Arg Val Lys Asp Gly
385                 390                 395                 400

Asp Val Pro Tyr Ile Cys Leu Asp Leu Val Tyr Gln Tyr Thr Leu Leu
                405                 410                 415

Val Asp Gly Phe Gly Ile Asp Pro Gln Gln Glu Ile Thr Leu Val Arg
            420                 425                 430

Gln Ile Gln Tyr Gln Asp Ser Leu Val Glu Ala Ala Trp Pro Leu Gly
        435                 440                 445

Ser Ala Ile Glu Ala Ile Ser Ser Leu Pro Lys Phe Glu Lys Leu Met
    450                 455                 460

Tyr Phe Leu
465
```